US006120776A

United States Patent [19]

Hasløv et al.

[11] Patent Number: 6,120,776

[45] Date of Patent: Sep. 19, 2000

[54] DIAGNOSTIC SKIN TEST FOR TUBERCULOSIS

[75] Inventors: Kaare Hasløv, Søborg; Åse Bengaard Andersen, Brønshøj; Thomas Oettinger, Hellerup, all of Denmark

[73] Assignee: Statens Seruminstitut, Copenhagen, Denmark

[21] Appl. No.: 08/569,221

[22] PCT Filed: Jun. 30, 1994

[86] PCT No.: PCT/DK94/00270

§ 371 Date: Feb. 12, 1996

§ 102(e) Date: Feb. 12, 1996

[87] PCT Pub. No.: WO95/01440

PCT Pub. Date: Jan. 12, 1995

[30] Foreign Application Priority Data

Jul. 2, 1993 [DK] Denmark .............................. 0797/93

[51] Int. Cl.[7] ......................... A61K 39/04; C12P 21/06; C12P 21/04; C12N 1/12

[52] U.S. Cl. .................... 424/248.1; 435/69.1; 435/69.3; 435/69.5; 435/253.1

[58] Field of Search ............................... 435/253.1, 69.1, 435/69.3, 69.51; 424/248.1

[56] References Cited

FOREIGN PATENT DOCUMENTS

WO 92/14823 9/1992 WIPO .

OTHER PUBLICATIONS

Man et al "treatment of human muscle creatine kinase with glutaraldehyde preferentially increases the immunogenicity of the native conformation and permits production of high–affinity monoclonal antibodies which recognize two distinct surface epitopes", J, Oct. 1, 1989.

Andersen et al "Proteins released from *Mycobacterium tuberculosis* during growth", Infection and Immunity, vol. 59, No. 6, pp. 1905–1910, Jun. 1, 1991.

A.B. Andersen et al., MPB64 Possesses Tuberculosis–Complex'–Specific B– and T–Cell Epitopes, Scand. J. Immunol. 34, 365–372, 1991.

Sadamu Nagai et al., Isolation and Partial Characterization of Major Protein Antigens in the Culture of *Mycobacterium tuberculosis*, Infection and Immunity, Jan. 1991, p. 373–382.

Anne Worsaee et al., Allergenic and Blastogenic Reactivity of Three Antigens from *Mycobacterium tuberculosis* in Sensitized Guinea Pigs, Infection and Immunity, Dec. 1987, p. 2922–2927.

Yamaguchi, Ryugi, et al., "Cloning and Characterization of the Gene for Immunogenic Protein MPB64 of *Mycobacterium bovis* BCG", *Infection and Immunity* 57(1):283–288 (1989).

Li, Huayi, et al., "Evidence for Absence of the MPB64 Gene in Some Substrains of *Mycobacterium bovis* BCG", *Infection and Immunity* 61(5):1730–1734 (1993).

Andersen, Å.B., et al., "Structure and Function of a 40,000–Molecular–Weight Protein Antigen of *Mycobacterium tuberculosis*", *Infection and Immunity* 60(6):2317–2323 (1992).

Wiker, H.G., et al., "A Family of Cross–Reacting Proteins Secreted by *Mycobacterium tuberculosis*", *Scand. J. Immunol.* 36:307–319 (1992).

Nagai, Sadamu, et al., "Isolation and Partial Characterization of Major Protein Antigens in the Culture Fluid of *Mycobacterium tuberculosis*", *Infection and Immunity* 59(1):372–382 (1991).

Leão, S.C., "Tuberculosis: New Strategies for the Development of Diagnostic Tests and Vaccines", *Brazilian J. Med. Biol. Res.* 26:827–833 (1993).

Oettinger, Thomas, et al., "Cloning and B–Cell–Epitope Mapping of MPT64 from *Mycobacterium tuberculosis* H37Rv", *Infection and Immunity* 62(5):2058–2064 (1994).

*Primary Examiner*—Rodney P. Swartz
*Attorney, Agent, or Firm*—Frommer Lawrence & Haug, LLP; Thomas J. Kowalski

[57] ABSTRACT

Diagnostic methods capable of discriminating between cell mediated immunologic responses due to on the one hand active tuberculosis caused by bacteria belonging to the tuberculosis complex (*Mycobacterium tuberculosis, Mycobacterium africanum* and *Mycobacterium bovis*) and on the other hand vaccination with an immunogenic agent conferring immunity to tuberculosis. A diagnostic kit is also provided, comprising a polypeptide (e.g. MPT64) capable of eliciting a delayed type hypersensitivity reaction (Dth) in animals with active tuberculosis, but not in animals vaccinated against TB with an immunogenic agent (e.g. *M. bovis* BCG strain: Danish 1331). Also provided are polypeptide fragments comprising a T-cell epitope of MPT64 as well as nucleic acid fragments encoding these polypeptide fragments.

50 Claims, 18 Drawing Sheets

MPT64-9→
▽1
TCTGCTAGCTTGAGTCTGGTCAGGCATCGTCGTCAGCAGCGCGATGCCCCTATGTTTGTC
                         -10                      -35

61
GTCGACTCAGATATCGCGGCAATCCAATCTCCCGCCTGCGCCGGCGGTGCTGCAAACTAC

121
TCCCGGAGGAATTTCGACGTGCGCATCAAGATCTTCATGCTGGTCACGGCTGTCGTTTTG
     SD          fMetArgIleLysIlePheMetLeuValThrAlaValValLeu
                 ↑
181                      MPT64-1→
                         ▽
CTCTGTTGTTCGGGTGTCGCCACGGCCGCGCCCAAGACCTACTGCGAGGAGTTGAAAGGC
LeuCysCysSerGlyValAlaThrAlaAlaProLysThrTyrCysGluGluLeuLysGly
                    ↑
241
ACCGATACCGGCCAGGCGTGCCAGATTCAAATGTCCGACCCGGCCTACAACATCAACATC
ThrAspThrGlyGlnAlaCysGlnIleGlnMetSerAspProAlaTyrAsnIleAsnIle

301                          MPT64-4→
                             ▽
AGCCTGCCCAGTTACTACCCCGACCAGAAGTCGCTGGAAAATTACATCGCCCAGACGCGC
SerLeuProSerTyrTyrProAspGlnLysSerLeuGluAsnTyrIleAlaGlnThrArg

361
GACAAGTTCCTCAGCGCGGCCACATCGTCCACTCCACGCGAAGCCCCCTACGAATTGAAT
AspLysPheLeuSerAlaAlaThrSerSerThrProArgGluAlaProTyrGluLeuAsn
                                                          MPT
421                                                       64-5→
                                                          ▽
ATCACCTCGGCCACATACCAGTCCGCGATACCACCGCGTGGTACGCAGGCCGTGGTGCTC
IleThrSerAlaThrTyrGlnSerAlaIleProProArgGlyThrGlnAlaValValLeu

481            ←MPT64-3                        StuI
               ▽                               ▽
AAGGTCTACCAGAACGCCGGCGGCACGCACCCAACGACCACGTACAAGGCCTTCGATTGG
LysValTyrGlnAsnAlaGlyGlyThrHisProThrThrThrTyrLysAlaPheAspTrp
  MPT64-6→
  ▽
541
GACCAGGCCTATCGCAAGCCAATCACCTATGACACGCTGTGGCAGGCTGACACCGATCCG
AspGlnAlaTyrArgLysProIleThrTyrAspThrLeuTrpGlnAlaAspThrAspPro

601                              MPT64-7→
                                 ▽
CTGCCAGTCGTCTTCCCCATTGTGCAAGGTGAACTGAGCAAGCAGACCGGACAACAGGTA
LeuProValValPheProIleValGlnGlyGluLeuSerLysGlnThrGlyGlnGlnVal
   ClaI
   ▽
661                    MPT64-8→
                       ▽
TCGATAGCGCCGAATGCCGGCTTGGACCCGGTGAATTATCAGAACTTCGCAGTCACGAAC
SerIleAlaProAsnAlaGlyLeuAspProValAsnTyrGlnAsnPheAlaValThrAsn

721              SmaI
                 ▽
GACGGGGTGATTTTCTTCTTCAACCCGGGGGAGTTGCTGCCCGAAGCAGCCGGCCCAACC
AspGlyValIlePhePhePheAsnProGlyGluLeuLeuProGluAlaAlaGlyProThr

781                                            ←MPT64-2
                                               ▽
CAGGTATTGGTCCCACGTTCCGCGATCGACTCGATGCTGGCCTAGA
GlnValLeuValProArgSerAlaIleAspSerMetLeuAlaEnd

Fig. 1

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| A1 | | | Q | A | Y | R | K | P | I | T | Y | D | T | L | W | Q | A | D | T | D | P | L | P | V | V | F | P | I |
| A2 | | | P | I | T | Y | D | T | L | W | Q | A | D | T | D | P | L | P | V | V | F | P | I | V | Q | G | E | |
| A3 | | | T | L | W | Q | A | D | T | D | P | L | P | V | V | F | P | I | V | Q | G | E | L | S | K | Q | T | |
| A4 | | | D | T | D | P | L | P | V | V | F | P | I | V | Q | G | E | L | S | K | Q | T | G | Q | Q | V | S | |
| B1 | | | P | V | V | F | P | I | V | Q | G | E | L | S | K | Q | T | G | Q | Q | V | S | I | A | P | N | A | |
| B2 | | | I | V | Q | G | E | L | S | K | Q | T | G | Q | Q | V | S | I | A | P | N | A | G | L | D | P | V | |
| B3 | | | L | S | K | Q | T | G | Q | Q | V | S | I | A | P | N | A | G | L | D | P | V | N | Y | Q | N | F | |
| B4 | | | G | Q | Q | V | S | I | A | P | N | A | G | L | D | P | V | N | Y | Q | N | F | A | V | T | N | D | |
| C1 | | | I | A | P | N | A | G | L | D | P | V | N | Y | Q | N | F | A | V | T | N | D | G | V | I | F | F | |
| C2 | | | G | L | D | P | V | N | Y | Q | N | F | A | V | T | N | D | G | V | I | F | F | F | N | P | G | E | |
| C3 | | | N | Y | Q | N | F | A | V | T | N | D | G | V | I | F | F | F | N | P | G | E | L | L | P | E | A | |
| C4 | | | A | V | T | N | D | G | V | I | F | F | F | N | P | G | E | L | L | P | E | A | A | G | P | T | Q | |
| D1 | | | G | V | I | F | F | F | N | P | G | E | L | L | P | E | A | A | G | P | T | Q | V | L | V | P | R | |
| D2 | | | F | N | P | G | E | L | L | P | E | A | A | G | P | T | Q | V | L | V | P | R | S | A | I | D | S | |
| D3 | | | L | L | P | E | A | A | G | P | T | Q | V | L | V | P | R | S | A | I | D | S | M | L | A | | | |
| D4 | | | | | | | | | | | | | | | | | | | | | | | | | | | | |

Fig. 15

DIAGNOSTIC SKIN TEST FOR TUBERCULOSIS

The present invention relates to a kit comprising as one part of the kit a vaccine containing as the effective component an immunogenic agent (e.g. mycobacteria from the BCG strain: Danish 1331) capable of conferring substantially increased immunity to tuberculosis, and as the other part of the kit at least one diagnostic skin test comprising a pharmaceutical composition containing a polypeptide with which lymphoid cells previously primed with mycobacteria belonging to the tuberculosis-complex are capable of reacting and with which lymphoid cells previously primed with the immunogenic agent are not capable of reacting, or a variant which is immunologically equivalent to the polypeptide, as well as a method of diagnosing tuberculosis caused by *Mycobacterium tuberculosis, Mycobacterium africanum* or *Mycobacterium bovis* in a person, comprising intradermally injecting, in the person, the skin test, a positive skin response at the location of injection being indicative of the person having or having had tuberculosis, and a negative skin response at the location of injection being indicative of the person not having or not having had tuberculosis, the polypeptide preferably being MPT64 or an immunologically equivalent variant, analogue or subsequence thereof. The invention further relates to a pharmaceutical composition comprising the polypeptide, a DNA fragment encoding a polypeptide which is an immunological equivalent to MPT64, the polypeptide which is an immunological equivalent to MPT64, as well as a method for vaccinating one or more persons in a population and subsequently subjecting the population to a diagnostic test for tuberculosis by the method described above.

BACKGROUND

Tuberculosis remains a major world health problem. In fact, the incidence is increasing in both the so-called developing part of the world as well as in industrialized countries like the United States of America. Recently, tuberculosis was ranked by the World Health Organization as the most frequent cause of death ascribable to a single infectious agent (Memorandum from a WHO meeting: Tuberculosis control and research strategies for the 1990s. Bulletin of the World Health Organization 70:17–21, 1992).

The means to effectively intervene transmission and thereby ultimately to get the disease under control are based on early diagnosis and treatment combined with vaccination of the populations at risk. The currently available anti-tuberculosis vaccine was developed in the beginning of this century by Calmette and Guérin and is often referred to as "the Bacille Calmette et Guérin (BCG)". The vaccine strain evolved after serial passages of a virulent isolate of *M. bovis* on a bile containing growth medium. The resultant strain appeared to be avirulent for humans. The nature of the loss of virulence is still not clearly understood at the molecular level. However, the BCG vaccine is estimated to be the most widely used live vaccine in the world and the remarkable low number of serious complications observed as a consequence of the use of BCG clearly demonstrate that the strain is fully attenuated (Lotte et al., Adv. Tuberc. Res. 21, 107–193 (1984)). When the reports of the first successful vaccinations were published, several laboratories and vaccine producers around the world requested the strain from Calmette and Guérin and the strain was subcultured locally under conditions which varied from one laboratory to another. This is the historical background for the occurrence of several substrains of BCG. Modern BCG producers make use of freeze-lot systems which ensure that the genetic composition of the bacteria—the product—has been conserved. Despite the widely accepted use of the BCG vaccine in many countries some countries never introduced it for use in general population vaccination programmes. This is the case in e.g. USA and Belgium. One of the reasons for these countries to be reluctant is that vaccination with BCG interferes with the use of tuberculin skin testings for diagnosing tuberculosis and for use in population surveys.

Infection of humans or susceptible animals with *M. tuberculosis* (or vaccination with BCG) will lead to the activation of the cellular branch of the immune system. The immunological status of a person (or animal) may therefore be monitored by analyses designed to measure the level of lymphoid cells primed against mycobacterial antigens. This may be done in vivo by measuring the "delayed type hypersensitivity (Dth) reaction" occurring 24 to 96 hours after the intracutaneous injection of mycobacterial antigen.

The product which is currently used for elicitation of Dth reactions is tuberculin—purified protein derivative (PPD). PPD consist of a crude mixture of proteins from *M. tuberculosis.* The proteins are recovered from synthetic medium which has supported growth of the bacteria from 5 to 6 weeks. The proteins are recovered by either ammonium sulphate or trichloric acetic acid precipitation after heat inactivation and removal of the bacterial bodies from the cultures. Contaminating lipids may be removed by ether extraction and low molecular components (<10,000) are removed by ultrafiltration. However, the structural composition of virulent mycobacteria belonging to the tuberculosis complex (i.e. *M. tuberculosis, M. bovis,* and *M. africanum*) and the attenuated BCG strain is so closely related that the currently available PPD, due to cross-reactivity, will elicit a positive reaction in a large fraction of the vaccinated population. PPD is not a species specific reagent and positive reactions may also be observed when people have been exposed to or infected with other mycobacterial species.

However, other reagents have been suggested as possible reagents in a skin test for diagnosing tuberculosis. From WO 92/21697 a diagnostic skin test which comprises a 38 kDa lipoprotein or a 19 kDa from *Mycobacterium tuberculosis* is known. The skin test has specificity for *Mycobacterium tuberculosis* infections, however, the skin test cannot distinguish between patients immunised with BCG and patients suffering from tuberculosis.

Furthermore, several mycobacterial proteins, e.g. MPT70 and MPT80 from Mycobacterium tuberculosis, as well as MPB64 from *Mycobacterium bovis* have been shown to elicit a Dth reaction in guinea pigs sensitized with mycobacteria belonging to the tuberculosis-complex. The gene encoding MPB64 has been cloned and sequenced (Yamaguchi et al. 1989) from *M. bovis* BCG Tokyo.

BRIEF DESCRIPTION OF THE INVENTION

It is an object of the invention to provide a kit comprising a vaccine for immunizing a person against tuberculosis and furthermore comprising a diagnostic skin test, whereby the immune status of the person with respect to tuberculosis may be assessed before the vaccination or periodically after the vaccination, the latter without having a positive response in the diagnostic test due to the immunization caused by the vaccination itself.

Accordingly, the present invention relates to a kit for sequential use comprising as one part of the kit a vaccine for immunizing a person against tuberculosis caused by *Mycobacterium tuberculosis, Mycobacterium africanum* or *Myco-*

*bacterium bovis* (=the tuberculosis complex), the vaccine comprising as the effective component an amount of an immunogenic agent effective in conferring substantial immunity to tuberculosis, and as the other part of the kit at least one diagnostic skin test comprising a pharmaceutical composition containing a polypeptide with which lymphoid cells previously primed with mycobacteria belonging to the tuberculosis-complex are capable of reacting and with which lymphoid cells previously primed with the immunogenic agent are not capable of reacting, or a variant which is immunologically equivalent to the polypeptide.

By the term "immunogenic agent" is meant any substance, composition of matter, or composition of organic material as for example a suspension of cells or cell components, the immunogenic agent being capable of conferring substantial immunity to tuberculosis in an animal, e.g. a human being, when administered in a suitable concentration/amount and in admixture with suitable substances.

It will be understood that according to the invention T-cells primed with this immunogenic agent should not react with a polypeptide capable of reacting with T-cells primed with mycobacteria belonging to the tuberculosis complex. The existence of such pairs of an immunogenic agent and a polypeptide has for the first time been demonstrated by the inventors and makes possible the distinction between vaccinated individuals and individuals with active tuberculosis.

An example of an immunogenic agent the properties described above is *Mycobacterium bovis* BCG Copenhagen, from the Copenhagen BCG Laboratory, Statens Seruminstitut, Denmark, as described in table 2, example 5; this BCG strain is hereinafter designated "BCG strain: Danish 1331". Together with the protein MPT64, BCG strain: Danish 1331 forms such a pair. However, it is highly likely that other mycobacterial strains or compositions comprised of components derived from mycobacteria will exhibit substantially the same immunological properties as BCG strain: Danish 1331, and such strains or compositions are also a part of the kit according to the invention.

Examples of strains which are likely to share the properties of *M. bovis* BCG strain: Danish 1331 are *M. bovis* BCG Glaxo, *M. bovis* BCG Pasteur, *M. bovis* BCG Canadian, and *M. bovis* BCG Tice. This is apparent from the results in example 5, where it was found that the gene encoding MPT64 apparently was lacking in these strains.

However, according to all aspects of the invention, BCG strain: Danish 1331 is especially preferred as the immunogenic agent employed.

By stating that an agent "confers substantial immunity to tuberculosis" is meant that the vaccination of a person with a vaccine comprising the agent results in a substantially increased resistance to diseases caused by infections with bacteria belonging to the tuberculosis complex. Examples of such vaccines are well-known in the art, and a vaccine containing BCG strain: Danish 1331 exhibits these properties as does vaccines containing other BCG strains.

By the term "polypeptide" is herein meant short peptides with a length of at least two amino acid residues and at most 10 amino acid residues, oligopeptides (11–100 amino acid residues), and longer peptides (the usual interpretation of "polypeptide", i.e. more than 100 amino acid residues in length) as well as proteins (the functional entity comprising at least one peptide, oligopeptide, or polypeptide which may be chemically modified by being glycosylated, by being lipidated, or by comprising prosthetic groups). The definition of polypeptides also comprises native forms of peptides/proteins in mycobacteria as well as recombinant proteins or peptides in any type of expression vectors transforming any kind of host, and also chemically synthesized peptides.

Furthermore, another object of the invention is a method of diagnosing tuberculosis, the method not resulting in positive responses in persons previously vaccinated against tuberculosis but not actively infected with mycobacteria belonging to the tuberculosis complex.

Accordingly, another aspect of the invention is a method of diagnosing tuberculosis (active or previous) caused by *Mycobacterium tuberculosis, Mycobacterium africanum* or *Mycobacterium bovis* in a person, comprising intradermally injecting, in the person, a pharmaceutical composition containing a polypeptide with which lymphoid cells previously primed with mycobacteria belonging to the tuberculosis complex are capable of reacting and with which lymphoid cells previously primed with the above-discussed immunogenic agent are not capable of reacting, or a variant which is immunologically equivalent to the polypeptide, a positive skin response at the location of injection being indicative of the person having or having had tuberculosis, and a negative skin response at the location of injection being indicative of the person not having or not having had tuberculosis.

In another aspect the present invention relates to a pharmaceutical composition for diagnosing tuberculosis containing a polypeptide with which lymphoid cells previously primed with mycobacteria belonging to the tuberculosis complex are capable of reacting and with which lymphoid cells previously primed with an immunogenic agent as discussed above are not capable of reacting, or a variant of the polypeptide which is immunologically equivalent to the polypeptide.

A further aspect of the invention is a DNA fragment comprising a subsequence or an analogue or a variant of the nucleotide sequence shown in SEQ ID NO: 1 (also shown in FIG. 1), the subsequence, analogue or variant encoding a polypeptide which is immunologically equivalent to the polypeptide encoded by the DNA sequence shown in SEQ ID NO: 1.

By the terms "analogue" or "variant" with regard to the DNA fragments of the invention is intended to indicate a nucleotide sequence which encodes a polypeptide exhibiting identical or substantially identical immunological properties to a polypeptide encoded by a DNA fragment of the invention shown in SEQ ID NO: 1.

It is well known that the same amino acid may be encoded by various codes, the codon usage being related, inter alia, to the preference of the organisms in question expressing the nucleotide sequence. Thus, one or more nucleotides or codons of a DNA fragment of the invention may be exchanged by others which, when expressed, result in a polypeptide identical or substantially identical to the polypeptide encoded by the DNA fragment in question.

Therefore, the terms "analogue" and "variant" are used in the present context to indicate a DNA fragment or a DNA sequence of a similar nucleotide composition or sequence as the DNA sequence encoding the amino acid sequence constituting MPT64, allowing for minor variations which do not have an adverse effect on the ligand binding properties and/or biological function and/or immunogenicity as compared to MPT64, or which give interesting and useful novel binding properties or biological functions and immunogenicities etc. of the analogue. The analogous DNA fragment or DNA sequence may be derived from an animal or a human or may be partially or completely of synthetic origin as described above. The analogue may also be derived through the use of recombinant DNA techniques.

Furthermore, the terms "analogue" and "subsequence" are intended to allow for variations in the sequence such as substitution, insertion (including introns), addition, deletion and rearrangement of one or more nucleotides, which variations do not have any substantial effect on the polypeptide encoded by a DNA fragment or a subsequence thereof. The term "substitution" is intended to mean the replacement of one or more nucleotides in the full nucleotide sequence with one or more different nucleotides, "addition" is understood to mean the addition of one or more nucleotides at either end of the full nucleotide sequence, "insertion" is intended to mean the introduction of one or more nucleotides within the full nucleotide sequence, "deletion" is intended to indicate that one or more nucleotides have been deleted from the full nucleotide sequence whether at either end of the sequence or at any suitable point within it, and "rearrangement" is intended to mean that two or more nucleotide residues have been exchanged with each other.

The variant or analogue of the DNA fragment in SEQ ID NO: 1 is preferably one that hybridizes under stringent hybridization conditions which are to be understood in their conventional meaning, i.e. that hybridization is carried out at 65° C. in 2×SSC and final washing at 65° C. in 1×SSC using the method specified in the "Preamble" part of the Examples below.

In yet another aspect, the invention relates to a polypeptide having an amino acid sequence comprising a subsequence, an analogue or a variant of the amino acid sequence shown in SEQ ID NO: 2, the polypeptide being immunologically equivalent to the polypeptide having the amino acid sequence shown in SEQ ID NO: 2.

By the terms "analogue", "variant" and "subsequence" when used in connection with polypeptides is meant any polypeptide having the same immunological characteristics as MPT64 with respect to being capable of discriminating between infection with mycobacteria of the tuberculosis complex and vaccination with BCG strain: Danish 1331. Thus, included is also a polypeptide from different sources, such as other bacteria or even from eukaryotic cells.

The terms "analogue" and "variant" with regard to a polypeptide are also used in the present context to indicate a protein or polypeptide of a similar amino acid composition or sequence as the characteristic amino acid sequence shown in SEQ ID NO: 2, allowing for minor variations which do not have an adverse effect on the ligand binding properties and/or biological function and/or immunogenicity, or which may give useful novel binding properties or biological functions and immunogenicities etc. of the analogue. The analogous polypeptide or protein may be derived from other microorganisms and the analogue may also be derived through the use of recombinant DNA techniques.

As can be seen from the examples, a subsequence of the gene encoding MPT64 has been identified, a subsequence which most likely encodes a T-cell epitope responsible for the elicitation of the immunological response which can be read in a skin test. Thus, the polypeptide encoded by this DNA fragment (SEQ ID NO: 2, amino acids nos. 186–215) as well as polypeptides encoded by analogues and subsequences of this DNA fragment are preferred subsequences of the proteins of the invention, as are analogues and variants of the polypeptide subsequence. Of course, also the DNA fragment (SEQ ID NO: 1, nucleotides nos. 694–783) as well as analogues and subsequences encoding this polypeptide subsequence are preferred DNA fragments of the invention. Especially interesting are DNA fragments of the invention comprising multiple copies of the DNA fragment encoding the T-cell epitope as are polypeptides of the invention comprising multiple copies of T-cell epitopes, as these are suspected to possess superior immunological properties over single epitope variants of the polypeptide.

In the present context the term "immunologically equivalent" means that the polypeptide is functionally equivalent to the polypeptide having the amino acid sequence shown in SEQ ID NO: 2 with respect to its ability of eliciting a Dth reaction to an extent of at least 45% of the Dth reaction elicited by the polypeptide under the same conditions, such as at least 65%, more preferred 85%, measured as the diameter of the Dth reaction.

In yet another aspect, the invention relates to a replicable expression vector comprising the DNA fragment defined above. In the present context "replicable" means that the vector is able to replicate in a given type of host cell into which it has been introduced. Immediately up-stream of the sequence encoding the polypeptide, the DNA may be provided with a sequence encoding a signal peptide, the presence of which ensures secretion of the polypeptide expressed by host cells harbouring the vector, as well as a cell harbouring the vector.

Also, an aspect of the invention is a method of producing a polypeptide as defined above comprising inserting a DNA fragment as defined above into a vector which is able to replicate in a host cell, introducing the resulting recombinant vector into the host cell, culturing the host cell in an appropriate culture medium under appropriate conditions for expressing the polypeptide, and recovering the polypeptide from the host cell or culture medium.

The medium used to grow the cells may be any conventional medium suitable for the purpose. Furthermore, the polypeptide may be produced in a transgenic animal, e.g. a transgenic mammal producing the polypeptide in the milk.

The DNA sequence used in the method may have been modified by site-specific mutagensis, such as modified in that at least one nucleotide has been inserted, deleted, substituted or added to the sequence.

Furthermore, the present invention relates to a method of vaccinating one or more selected persons of a population against tuberculosis and subsequently subjecting the population to diagnostic tests for tuberculosis, comprising vaccinating the persons with a vaccine, which comprises as its effective component the above-discussed immunogenic agent, and subsequently subjecting the population to intradermal injection of pharmaceutical compositions containing a polypeptide with which lymphoid cells previously primed with mycobacteria from the tuberculosis complex are capable of reacting in vitro and with which lymphoid cells previously primed with the immunogenic agent are not capable of reacting or a variant which is immunologically equivalent to the polypeptide, whereby a positive skin response at the location of injection is indicative of the person having tuberculosis, and a negative skin response at the location of injection is indicative of the person not having tuberculosis, and to the use of a vaccine, which comprises as its effective component the above-discussed immunogenic agent (e.g. BCG strain: Danish 1331), for vaccinating, against tuberculosis, one or more persons of a population which subsequently is to be subjected to tuberculosis diagnosis using a diagnostic agent comprising a polypeptide with which lymphoid cells previously primed with mycobacteria from the tuberculosis complex are capable of reacting in vitro and with which lymphoid cells previously primed with the above-discussed immunogenic agent are not capable of reacting or a variant which is immunologically equivalent to the polypeptide.

By this method there is no risk that the vaccination interferes with the skin testing for diagnosing tuberculosis because with the combination of the BCG strain used for vaccine purpose and the diagnostic skin test, positive Dth reactions with only occur in persons suffering from tuberculosis, whereas no Dth reaction can be observed in persons previously vaccinated and not suffering from tuberculosis.

DETAILED DESCRIPTION OF THE INVENTION

Figure 2:
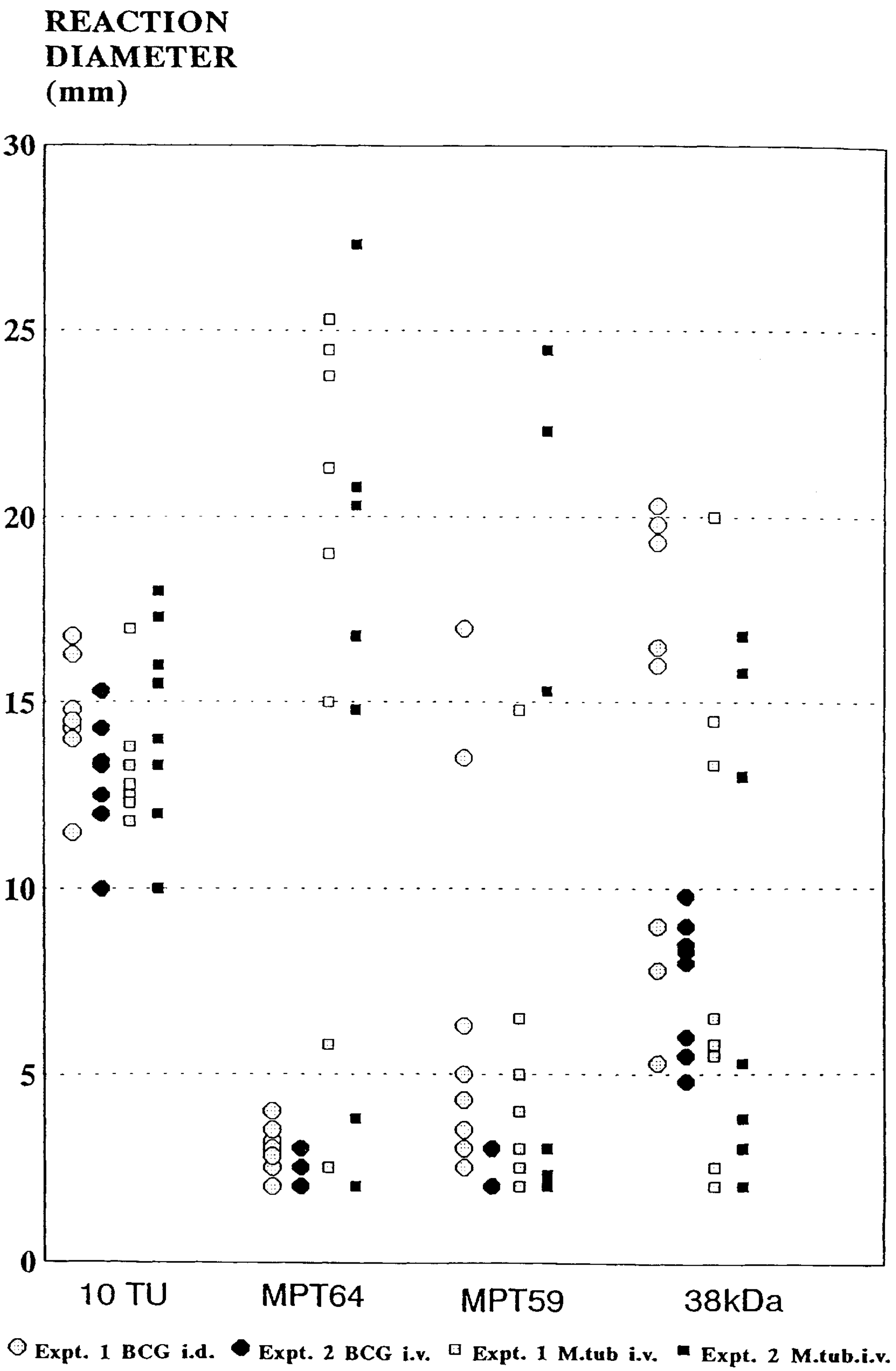

The importance of the polypeptide of the invention is its ability of eliciting a delayed type hypersensitivity (Dth) reaction in persons having active tuberculosis caused by virulent mycobacteria belonging to the tuberculosis complex, but not eliciting a Dth reaction in persons previously vaccinated with a vaccine comprising the above-discussed immunogenic agent, e.g. BCG strain: Danish 1331. The Dth reaction is an inflammatory reaction occurring in the subcutaneous environment exhibiting the cardinal features: erythema and induration due to cellular infiltration and edema. The diameter of this reaction is measured by visual inspection and use of a ruler.

The kit according to the invention will thus be useful in assessing a person's immune status with respect to tuberculosis before vaccination, either to diagnose tuberculosis or to diagnose that the person has been vaccinated with a vaccine different from the vaccine defined above. This is useful, e.g. at immigration camps where the immune status of the immigrant's are tested before they are allowed immigration.

Furthermore, the kit may be useful for vaccinating individuals of a population and subsequently follow their immune status with respect to tuberculosis infections, because the immunization caused by the vaccination does not give rise to a positive response to the skin test. Only persons having tuberculosis will have a positive response when subjected to the skin test. Vaccinated persons may be subjected to the skin test periodically, such as every year or every second year, but other intervals may also be suitable depending on the population to be tested.

In the present context the wording "immune status with respect to tuberculosis" means whether the person in question has a positive or negative immune response, when measured with the skin test of the present invention, which skin test is specific for tuberculosis infection and therefore gives a specific picture of their immune status, i.e. whether they have tuberculosis or not.

The kit may comprise several skin tests, such as 3 or 5 skin tests, whereby the kit may be used for several years after the vaccination.

Furthermore, by using the above defined method of diagnosing tuberculosis it is thus possible to follow disease transmission rate by skin testing surveys in populations by subjecting the persons of the population to a diagnostic skin test as defined above or as a diagnostic tool in individual cases, and thereby diagnose the person(s) suffering from active tuberculosis without having positive results from persons previously vaccinated and not having active tuberculosis. Thus, the polypeptide is one that is capable of reacting with lymphoid cells that previously have been primed with mycobacteria belonging to the tuberculosis complex and one that is not capable of reacting with lymphoid cells that previously have been primed with mycobacteria from the above-discussed immunogenic agent, e.g. BCG strain: Danish 1331. It is contemplated that this difference in reactivity between mycobacteria belonging to the tuberculosis complex and those belonging to the BCG strain: Danish 1331 is caused by the fact that virulent replicating mycobacteria belonging to the tuberculosis complex actively secrete a protein which is identical or immunologically equivalent to the polypeptide, whereas replicating mycobacteria from the BCG strain: Danish 1331 do not secrete the protein or secrete the protein in such a small amount that it cannot evoke a lymphoid immune response. However, mycobacteria from some of the other BCG strains used for vaccine purposes may induce reactions similar to mycobacteria from the BCG strain: Danish 1331 either because the mycobacteria do not secrete the protein or if they secrete the protein in sufficient amounts to evoke a lymphoid cell immune response, this immune response will not give rise to a persisting Dth reaction but fade out some time after the vaccination which in practice means that when vaccinated persons are tested no Dth reaction is elicited.

A method of measuring cellular immunity against the polypeptide, i.e. measuring whether the polypeptide reacts with lymphoid cells previously primed may be carried out either in an in vitro system or an in vivo system.

One in vitro system may be a lymphocyte proliferation assay. In this assay peripheral blood mononuclear cells from persons vaccinated with a vaccine comprising as its effective component the above-discussed immunogenic agent and from persons having tuberculosis are co-cultured for 4 to 5 days in the presence of the polypeptide as antigen. Immune lymphoid cells will proliferate in response to the antigenic stimulus and the proliferation is quantitated by the addition to the culture of 3-H thymidine which will be incorporated in the DNA during cell replication and measuring the amount of 3-H thymidine.

An in vivo system may be measurement of the Dth reaction occurring about 24 to 48 hours after intracutaneous or intradermal injection of mycobacterial antigen in a person or animal.

In the present context the term "immunologically equivalent variant, analogue or subsequence" means a variant, analogue or subsequence of the polypeptide, which is capable of reacting with lymphoid cells primed as described above and eliciting responses which are substantially identical to the responses elicited by the polypeptide itself, or eliciting responses which are at least 45% identical to the responses elicited by the polypeptide itself.

When the kit and the method of diagnosing tuberculosis is used, the skin response should be measured a few days after the intradermal injection has been performed. The skin response mostly appears 1–4 days after the injection, such as 2–3 days. If a skin response is observed and has waned before 24 hours have passed after the injection, it is mostly due to an irrelevant reaction which is not indicative of the person having tuberculosis.

The skin response is measured as described above by visual inspection and by the use of a ruler. A positive skin response is mostly between 0.5 cm and 4.0 cm in diameter, more often between 1.0 cm and 3.0 cm in diameter.

An effective skin response is only obtained if a sufficient amount of the polypeptide remains at the location of injection; however, the size of some polypeptides may be so small that the polypeptide diffuses rapidly in the extracellular compartment at the site of injection resulting in a less effective skin response. Consequently, as aspect of the present invention is a kit wherein the pharmaceutical composition comprises either a homopolymer or a heteropolymer of the polypeptide, whereby the polypeptide does not diffuse freely in the extracellular compartment and is efficiently taken up by antigen-presenting cells at the location.

A homopolymer of the polypeptide is to be understood in its usual meaning, i.e. a polymer formed by two or more identical polypeptides, whereas a heteropolymer may be formed by at least two different polypeptides, or formed by a polypeptide and a heterologous carrier molecule.

The homopolymer may be formed by 2 or more copies of the polypeptide, such as 2–20 copies or 2–10 copies, more preferred 2–6 copies.

An example of the synthesis of a homopolymer may be the introduction of one or more N-terminal cysteine residues in the polypeptide, thereby allowing the homopolymer to be formed as a result of intermolecular disulphide bridges.

The synthesis of a heteropolymer may be carried out by coupling the polypeptide to another mycobacterial polypeptide, such as the mycobacterial protein MPT59 or part thereof (The MPT59 protein is described in Nagai et al, Inf. and Imm. pp. 373–382, 1991).

By the synthesis of polymers of the polypeptide the specific activity or potency will increase because the polypeptide will not diffuse freely in the extracellular compartment, whereby a smaller dose of the polypeptide is necessary to elicit an observable Dth reaction.

Other kinds of modifications of the polypeptide may be relevant in order to increase the activity of it. Such modifications may be post-translational modifications such as acylation, i.e. addition of a lipid moiety, and/or glycosylation.

In the kit according to the invention the pharmaceutical composition comprises 0.05 to 20 $\mu$g of the polypeptide, such as 0.5 to 2.0 $\mu$g of the polypeptide, most preferred 0.75 to 1.5 $\mu$g of the polypeptide. When the pharmaceutical composition comprises polymers of the polypeptide the same amounts are suitable.

In a preferred embodiment of the invention the amino acid sequence of the polypeptide comprises an amino acid sequence which is homologous to the amino acid sequence shown in SEQ ID NO: 2, which is the sequence of MPT64, including the sequence of the signal peptide, or homologous to the amino acid sequence of an immunologically equivalent variant of the polypeptide.

MPT64 is a protein which is secreted and released from metabolizing mycobacteria, in particular mycobacteria from the tuberculosis complex.

MPT 64 has an amino acid sequence of 205 amino acids with a calculated molecular weight of 22,433.

The polypeptide may also be a variant of the polypeptide with the amino acid sequence shown in SEQ ID NO: 2, in that the amino acid sequence of the variant is homologous to an analogue or a subsequence of the amino acid sequence shown in SEQ ID NO: 2.

The term "homologous" is used here to illustrate the degree of identity between the amino acid sequence of a given polypeptide and the amino acid sequence shown in SEQ ID NO: 2. The amino acid sequence to be compared with the amino acid sequence shown in SEQ ID NO: 2 may be deduced from a DNA sequence, e.g. obtained by hybridization as defined above, or may be obtained by conventional amino acid sequencing methods. The degree of homology is preferably determined on the amino acid sequence of a mature polypeptide, i.e. without taking any leader sequence into consideration. It is preferred that the degree of homology is at least 80%, such as at least 90%, preferably at least 95% or even 98% with the amino acid sequence shown in SEQ ID NO: 2.

Each of the polypeptides may be characterized by specific amino acid and nucleic acid sequences. It is to be understood, however, that such sequences include analogues and variants produced by recombinant methods wherein such nucleic acid and polypeptide sequences have been modified by substitution, insertion, addition and/or deletion of one or more nucleotides in said nucleic acid sequences to cause the substitution, insertion, addition or deletion of one or more amino acid residues in the recombinant polypeptide. When the term DNA is used in the following, it should be understood that for the number of purposes where DNA can be substituted with RNA, the term DNA should be read to include RNA embodiments which will be apparent for the man skilled in the art.

In order to possess an ability of eliciting a Dth reaction a polypeptide must be at least 12 amino acids long, preferably at least 15 amino acids, such as 20 amino acids.

The polypeptide may have been encoded by a nucleotide sequence comprising a nucleotide sequence homologous to the nucleotide sequence shown in SEQ ID NO: 1, which is the nucleotide sequence encoding MPT64 or a variant or analogue or subsequence of the nucleotide sequence, the variant, analogue or subsequence encoding an immunologically effective equivalent to the polypeptide.

The variant or analogue refers to an nucleotide sequence wherein at least one nucleotide has been substituted, deleted, inserted or added either leading to a modified amino acid sequence or to the same amino acid sequence.

A nucleotide subsequence as used above refers to an effective subsequence which means that it encodes a polypeptide which is immunologically functional with respect to the ability of eliciting a Dth reaction. The subsequence may be the result of a truncation at either end of the DNA sequence and/or of the removal of one or more nucleotides or nucleotide sequences within DNA sequence.

Figure 10:
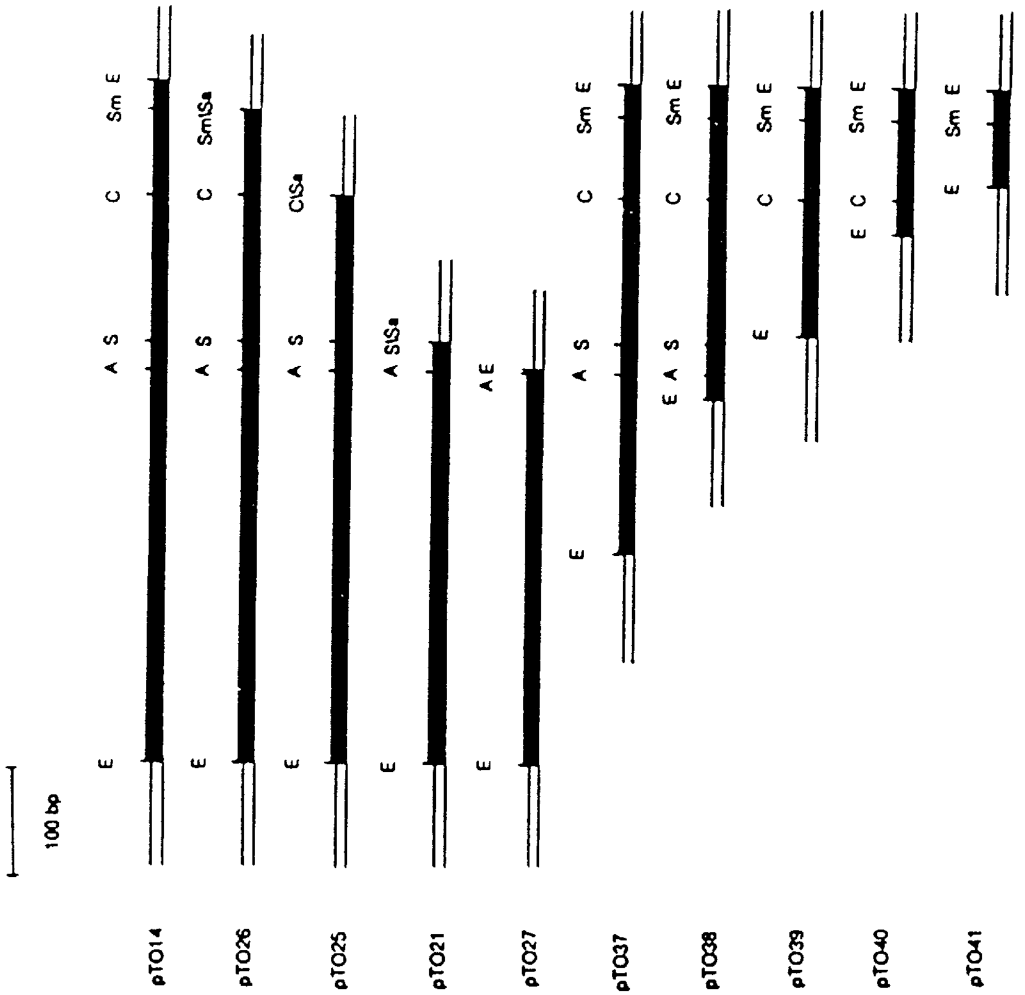

Interesting subsequences or deletion mutants are those shown in FIG. 10, and furthermore those constructed by use of the oligonucleotides shown in table 1 as primers in a PCR reaction as described in example 4.

The relevant functional parts of the polypeptide with respect to the ability of the polypeptide to elicit a Dth reaction are the lymphoid cell epitopes. i.e. the parts of the amino acid sequence that are recognized by lymphoid cells. These epitopes may either be linear or structural.

The injection of the polypeptide may lead to an undesired sensitization of the persons diagnosed for tuberculosis if the same person will be subjected to the skin test more than twice, or in extreme situations more than once.

Consequently, an object of the present invention is a kit wherein the polypeptide has been modified in order to abolish or delete sensitizing epitopes, without abolishing the epitopes that are relevant with respect to the Dth reactions.

This may be carried out by several methods well-known to the person skilled in the art. One method may be to modify the polypeptide by denaturing procedures, such as those selected from the group consisting of autoclaving or formaldehyde treatment.

Another method may be to modify the nucleotide sequence encoding the polypeptide in such a way that the translated amino acid sequence lacks all or some of the sensitizing epitopes.

In the present context the wording "sensitizing epitopes" means epitopes that cause sensitization of a person when the skin test has been used for diagnostic purposes. These epitopes may be either B-cell epitopes or T-cell epitopes.

Due to genetic variation persons may be divided into responders and non-responders to a specific polypeptide based on their ability of raising a lymphoid cell immune response to the polypeptide. Thus, for some polypeptides a skin test wherein only one polypeptide is present may give rise to false negative responses, i.e. negative responses even though the person is suffering from tuberculosis because the lymphoid cell immune system of the person has not been able to raise an immune response towards the polypeptide. Consequently, in a preferred embodiment of the present invention, the pharmaceutical composition comprises at least two different polypeptides either separated or as polymers as described above, all the polypeptides being as defined above.

One combination of polypeptides according to the invention is a pharmaceutical composition wherein one polypeptide is MPT64 or an immunologically effective equivalent thereto, and another polypeptide is MPT59 or an immunologically effective equivalent thereto.

A pharmaceutical composition according to the invention is a composition suitable for intradermal injection.

The DNA fragment of the invention comprises a subsequence or a analogue of the nucleotide sequence shown in SEQ ID NO: 1, the subsequence or analogue encoding a polypeptide which is immunologically equivalent to the polypeptide encoded by the DNA sequence shown in SEQ ID NO: 1.

The subsequence and analogue are intended to be understood as defined above.

Furthermore, a replicable expression vector comprising a DNA fragment as described above is an aspect of the invention.

The vector may be any vector which may conveniently be subjected to recombinant DNA procedures, and the choice of vector will often depend on the host cell into which it is to be introduced. Thus, the vector may be an autonomously replicating vectro, i.e. a vector which exists as an extrachromosomal entity, the replication of which is independent of chromosomal replication; examples of such a vector are a plasmid, phage, cosmid, mini-chromosome or virus. Alternatively, the vector may be one which, when introduced in a host cell, is integrated in the host cell genome and replicated together with the chromosome(s) into which it has been integrated.

The present invention further relates to a cell harbouring a replicable expression vector as defined above. In principle, this cell may be of any type of cell, i.e. a prokaryotic cell such as a bacterium, e.g. *E. coli,* a unicellular eukaryotic organism, a fungus or yeast, or a cell derived from a multicellular organism, e.g. an animal or a plant. It is especially in cases where glycosylation is desired that a mammalian cell is used, although glycosylation of proteins is a rare event in prokaryotes.

In further aspect the present invention relates to the polypeptide comprising an amino acid sequence which is different from but homologous to a subsequence, an analogue or a variant of the amino acid sequence shown in SEQ ID NO: 2, the polypeptide being immunologically equivalent to the polypeptide of the amino acid sequence shown in SEQ ID NO: 2, the degree of homology being as defined above.

Particularly interesting is a polypeptide which has been modified in order to abolish or delete B- or T-cell epitopes which may be sensitizing, without abolishing the epitopes that are relevant for the Dth reaction.

In a yet further aspect the present invention relates to a method of producing a polypeptide as defined above, by inserting a DNA fragment as defined above into a vector which is able to replicate in a host cell, introducing the resulting recombinant vector into the host cell, culturing the host cell in an appropriate culture medium under appropriate conditions for expressing the polypeptide, and recovering the polypeptide from the host cell or culture medium.

The medium used to grow the cells may be any conventional medium suitable for the purpose. A suitable vector may be any of the vectors described above, and an appropriate host cell may be any of the cell types listed above. The methods employed to construct the vector and effect introduction thereof into the host cell may be any methods known for such purposes within the field of recombinant DNA.

The DNA sequence to be modified may be of cDNA or genomic origin as discussed above, but may also be of synthetic origin. Furthermore, the DNA sequence may be of mixed cDNA and genomic, mixed cDNA and synthetic or genomic and synthetic origin as discussed above. The DNA sequence may have been modified, e.g. by site-directed mutagenesis, to result in the desired DNA fragment encoding the desired polypeptide. The following discussion focused around modifications of DNA encoding the polypeptide should be understood to encompass also such possibilities, as well as the possibility of building up the DNA by ligation of two or more DNA fragments to obtain the desired DNA fragment, and combinations of the above-mentioned principles.

The DNA sequence may be modified using any suitable technique which results in the production of a DNA fragment encoding a polypeptide of the invention.

The modification of the DNA sequence encoding the amino acid sequence of the polypeptide of the invention should be one which does not impair the immunological function of the resulting polypeptide.

Also, the polypeptide of the invention may be produced by the well-known methods of solid or liquid phase peptide synthesis utilizing the successive coupling of the individual amino acids of the polypeptide sequence or coupling of individual amino acids forming fragments of the polypeptide sequence so as to result in the desired polypeptide.

The design of skin test for diagnosing tuberculosis, which is closely related to a vaccine for vaccinating persons against tuberculosis, so that a minimum of false positive indication of tuberculosis are detected is an aim of the present invention. This has been fulfilled by the described kit comprising a skin test and a vaccine comprising as the effective component the above-discussed immunogenic agent, because the polypeptide of the method does not give rise to a Dth reaction in a person, if the person has been immunized with a vaccine comprising the immunogenic agent.

Consequently, an effective population survey may be conducted if the individuals of the population have been vaccinated with the described vaccine and the subsequent diagnostic tests are carried out by the methods as described.

Thus, an object of the invention is a method of vaccinating one or more selected persons of a population against tuberculosis and subsequently subjecting the population to diagnostic tests for tuberculosis, comprising vaccinating the persons with a vaccine, which comprises as its effective component the above-discussed immunogenic agent, and subsequently subjecting the population to intradermal injection of pharmaceutical compositions containing a polypeptide with which lymphoid cells previously primed with mycobacteria belonging to the tuberculosis complex are capable of reacting in vitro and with which lymphoid cells previously primed with the immunogenic agent are not capable of reacting or a variant which is immunologically equivalent to the polypeptide, whereby a positive skin response at the location of injection is indicative of the person having tuberculosis, and a negative skin response at the location of injection is indicative of the person not having tuberculosis.

Another object of the invention is the use of a vaccine which comprises as its effective component the above-discussed immunogenic agent for vaccinating, against tuberculosis, one or more persons of a population which subsequently are to be subjected to tuberculosis diagnosis using a diagnostic agent comprising a polypeptide with which lymphoid cells previously primed with mycobacteria belonging to the tuberculosis complex are capable of reacting in vitro and with which lymphoid cells previously primed with the immunogenic agent are not capable of reacting or a variant which is immunologically equivalent to the polypeptide.

LEGENDS TO FIGURES

FIG. 1: The sequence of the gene encoding MPT64 and the corresponding deduced amino acid sequence of MPT64. The first arrow indicates the start of the polypeptide including the signal sequence, the second arrow indicates the sequence of the mature protein when the signal sequence has been cleaved of. Furthermore, the start position of the oligonucleotide sequences shown in table 1 is shown, as well as the restriction sites discussed in example 4.

FIG. 2: The distribution of skin reactions to mycobacterial antigens.

Groups of 8 Ssc:AL guinea pigs were infected i.v. with *M. tuberculosis* H37Rv or with BCG strain: Danish 1331 given i.d. or i.v. Three weeks later guinea pigs were skin tested with 1 μg of the indicated purified antigens and with 10 T.U. of tuberculin.

Figure 3:
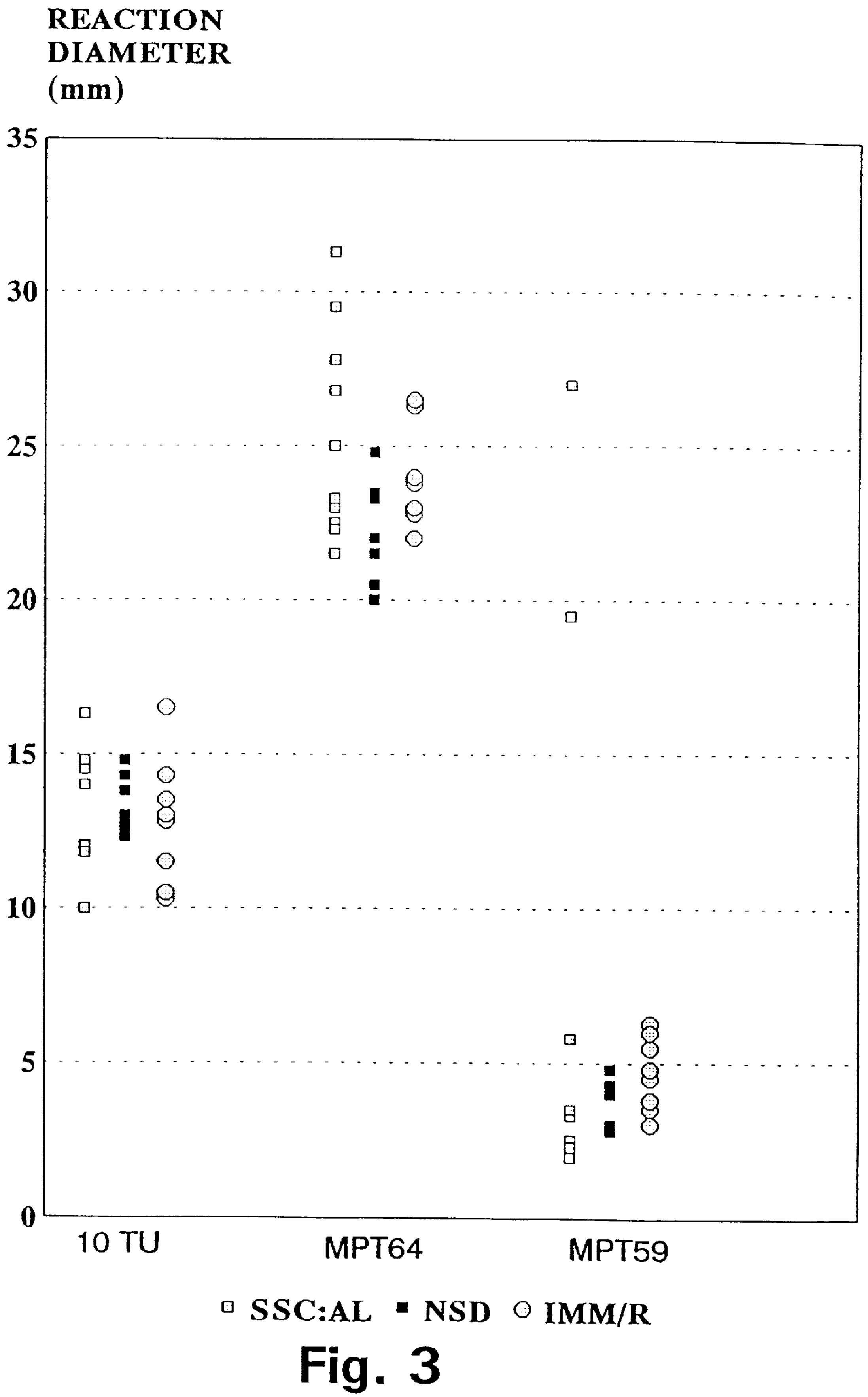

FIG. 3: The distribution of skin reactions to mycobacterial antigens.

Groups of guinea pigs of 8 Ssc:AL and of strains NSD and IMM/R were infected i.v. with *M. tuberculosis* R1609 and skin tested 3 weeks later with 1 μg of the indicated purified antigens and 10 T.U. of tuberculin.

Figure 4:
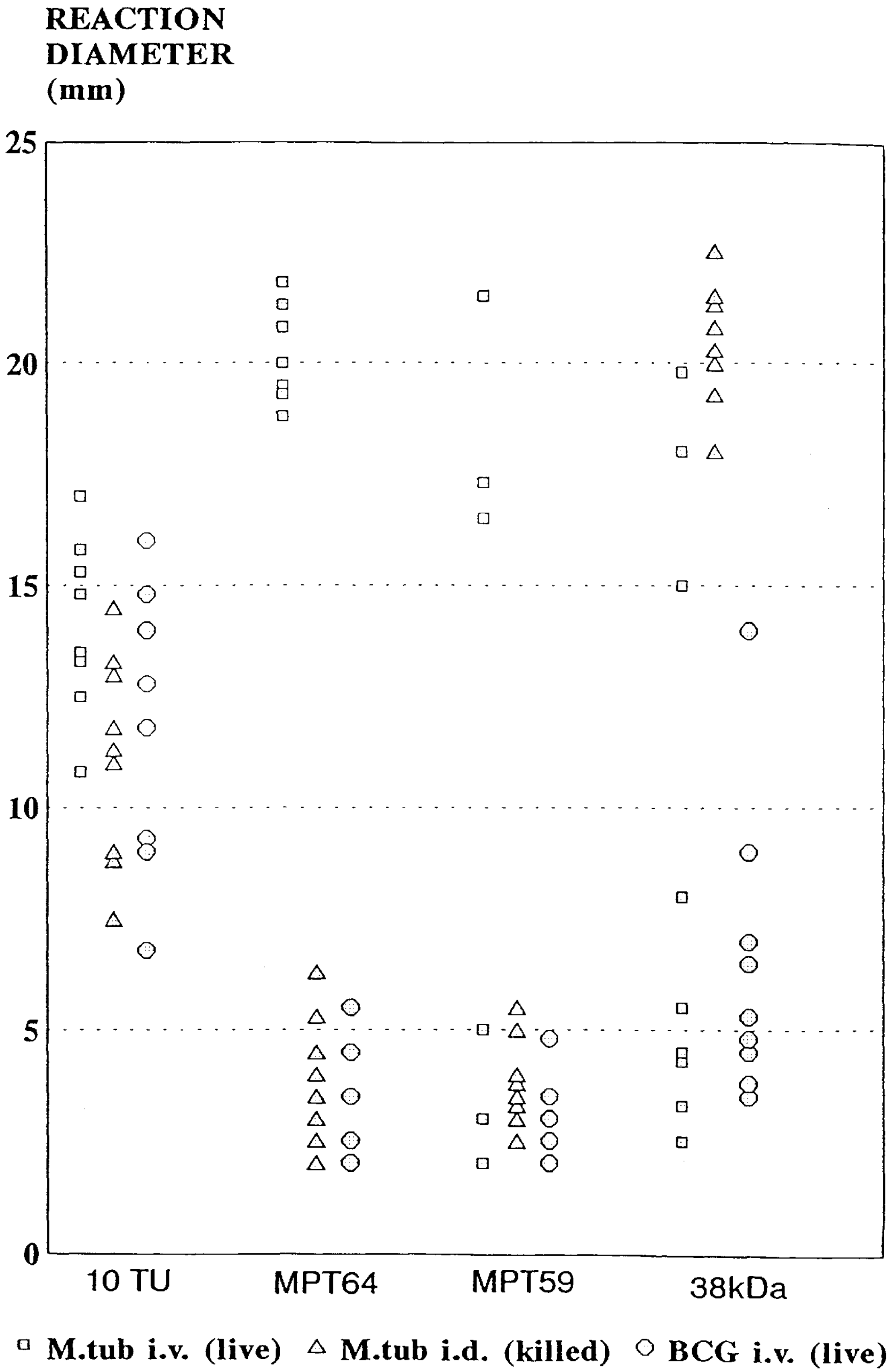

FIG. 4: The distribution of skin reactions to mycobacterial antigens.

Groups of 10 Ssc:AL guinea pigs were infected i.v. with *M. tuberculosis* H37Rv, BCG strain: Danish 1331 or immunized with killed *M. tuberculosis* in oil and skin tested 3 weeks later with 1 μg of the indicated purified antigens and 10 T.U. of tuberculin.

Figure 5:
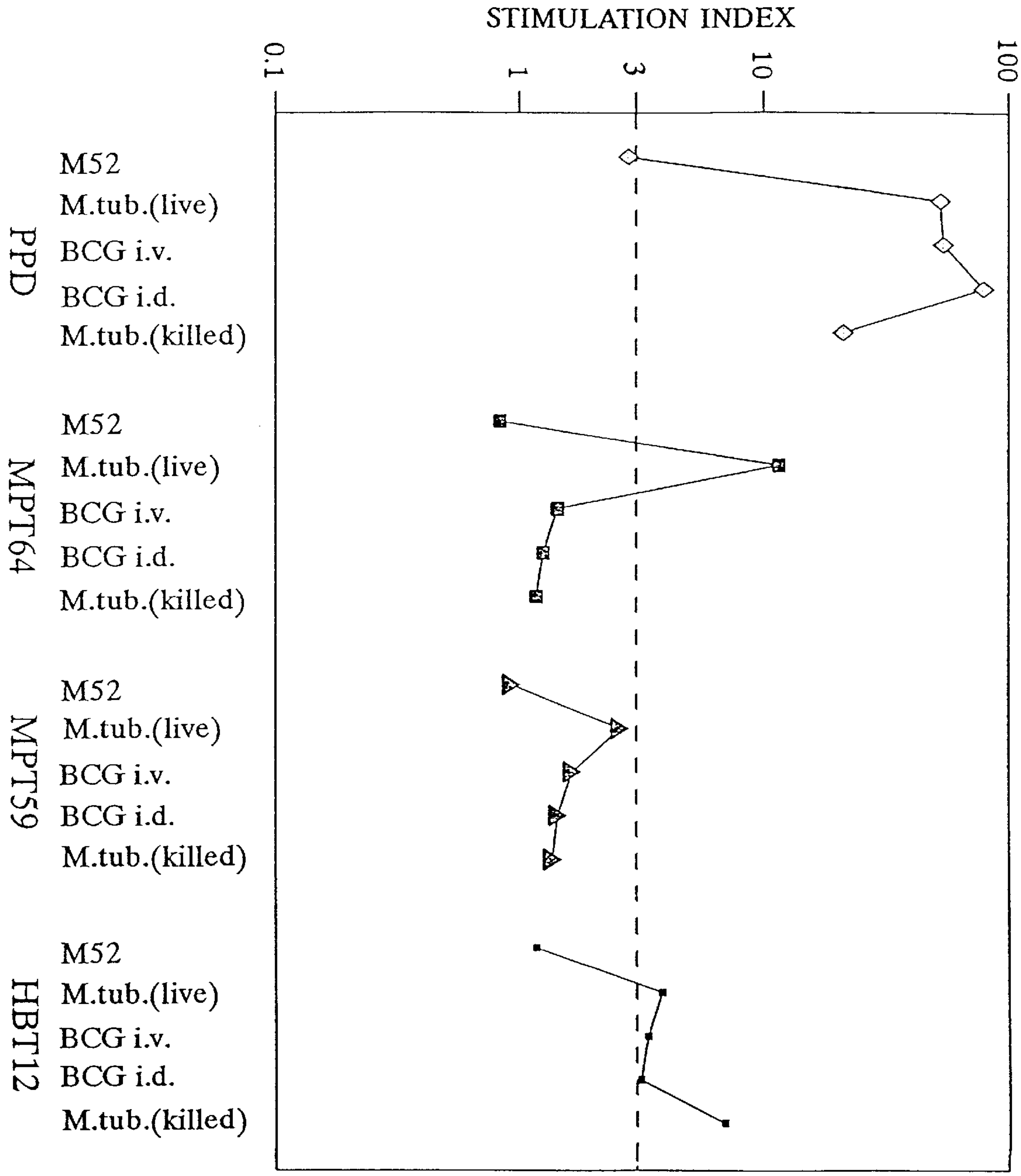

FIG. 5: The peripheral blood lymphocyte stimulation results to 1 μg of the mycobacterial preparations.

Groups of Ssc:AL guinea pigs were sensitized by infection with *M. tuberculosis* H37Rv, BCG, i.d., BCG i.v. or immunized with killed *M. tuberculosis* in oil or with the oil (M52) alone. HBT12 designates the 38 kDa antigen. Results are shown as means within immunization groups for stimulation indices. Indices above 3 are considered significant.

Figure 6:
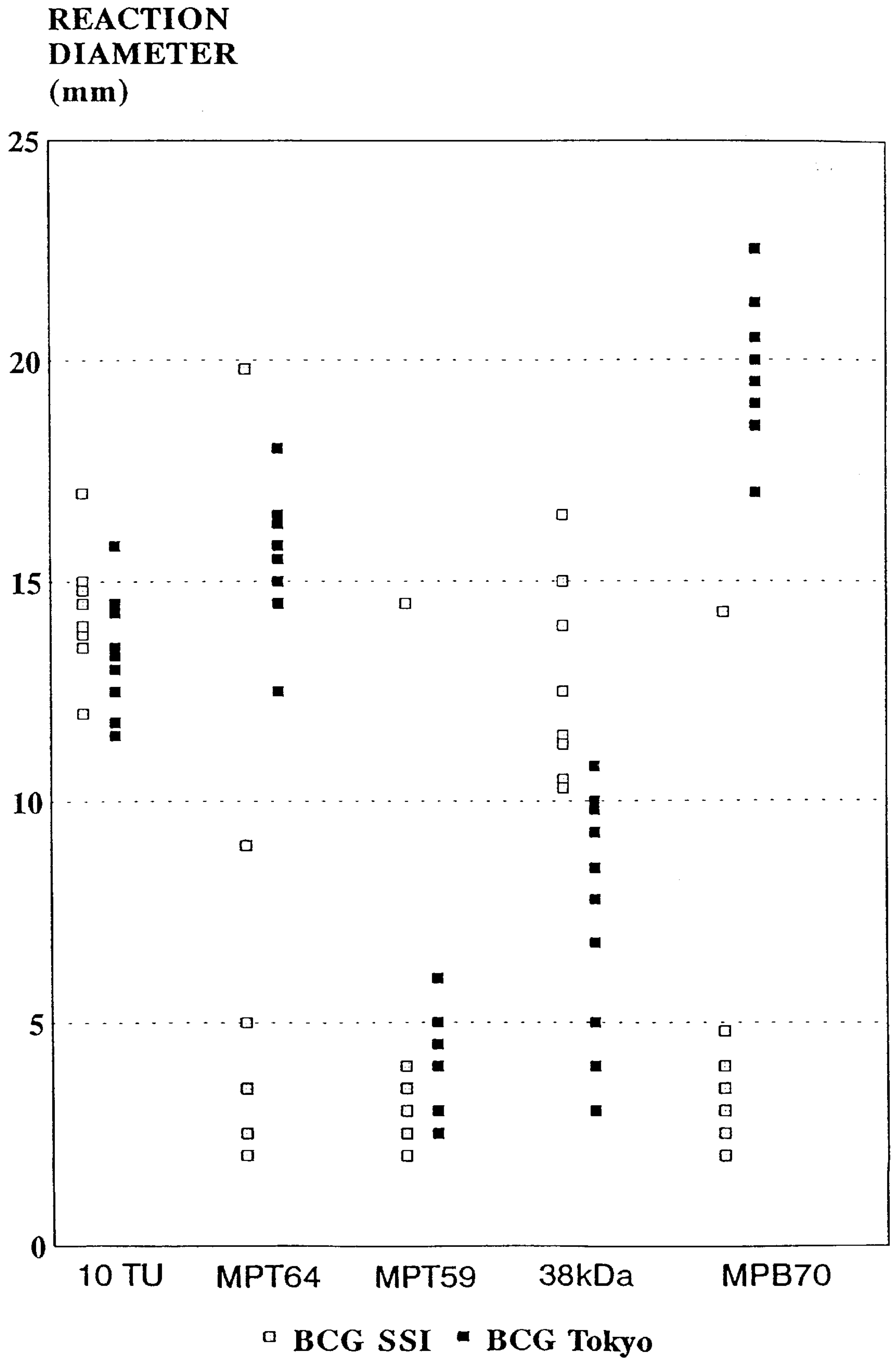

FIG. 6: The distribution of skin reactions to BCG antigens. Groups of 10 Ssc:AL guinea pigs were vaccinated i.d. with BCG strain: Danish 1331 or BCG Tokyo and skin tested 3 weeks later with 1 μg of the indicated purified antigens and 10 T.U. of tuberculin.

Figure 7:
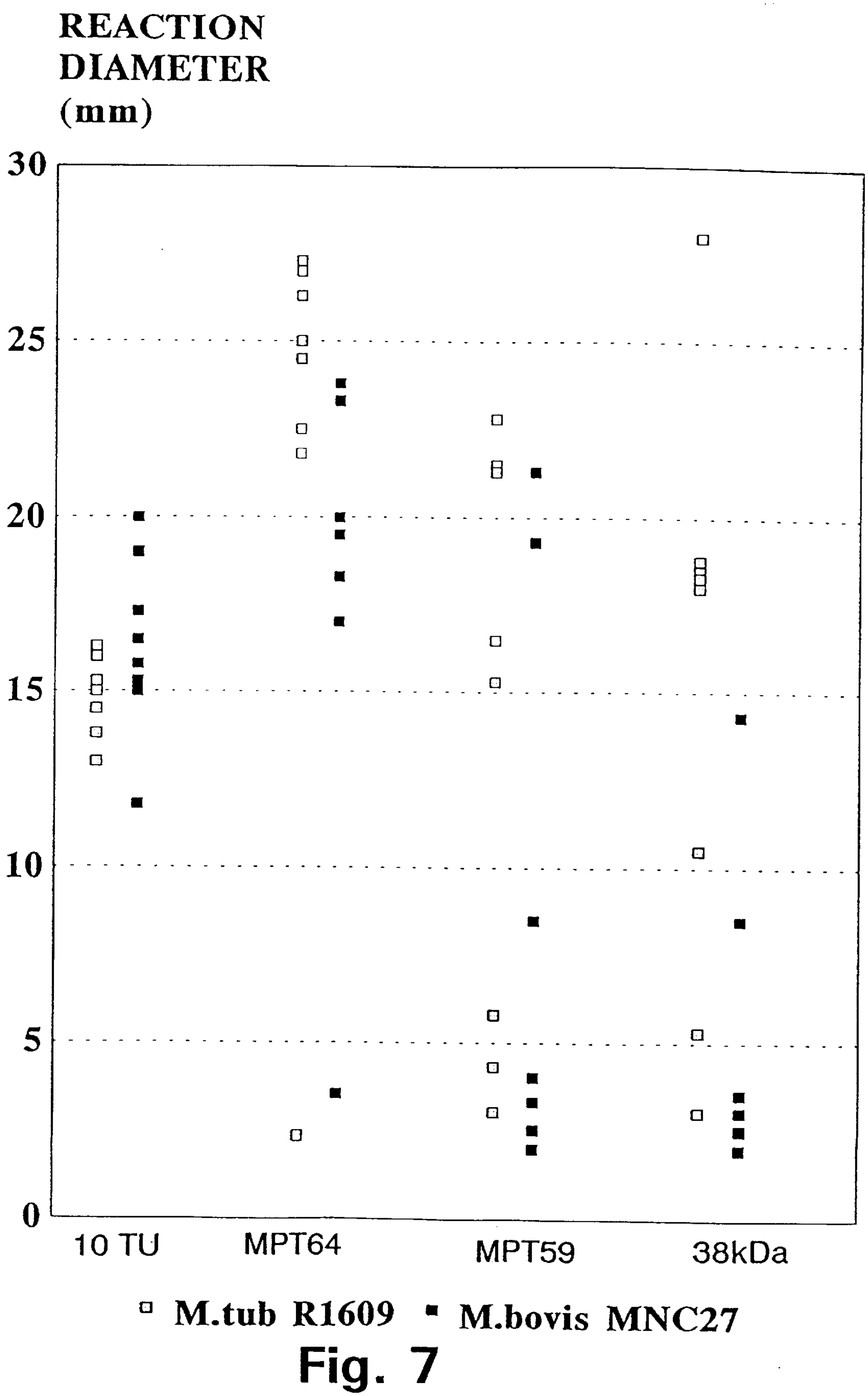

FIG. 7: The distribution of skin reactions to mycobacterial antigens.

Groups of 8 Ssc:AL guinea pigs were infected with *M. tuberculosis* R1609 or *M. bovis* MNC27 and skin tested 3 weeks later with 1 μg of the indicated purified antigens and with 10 T.U. of tuberculin.

Figure 8:
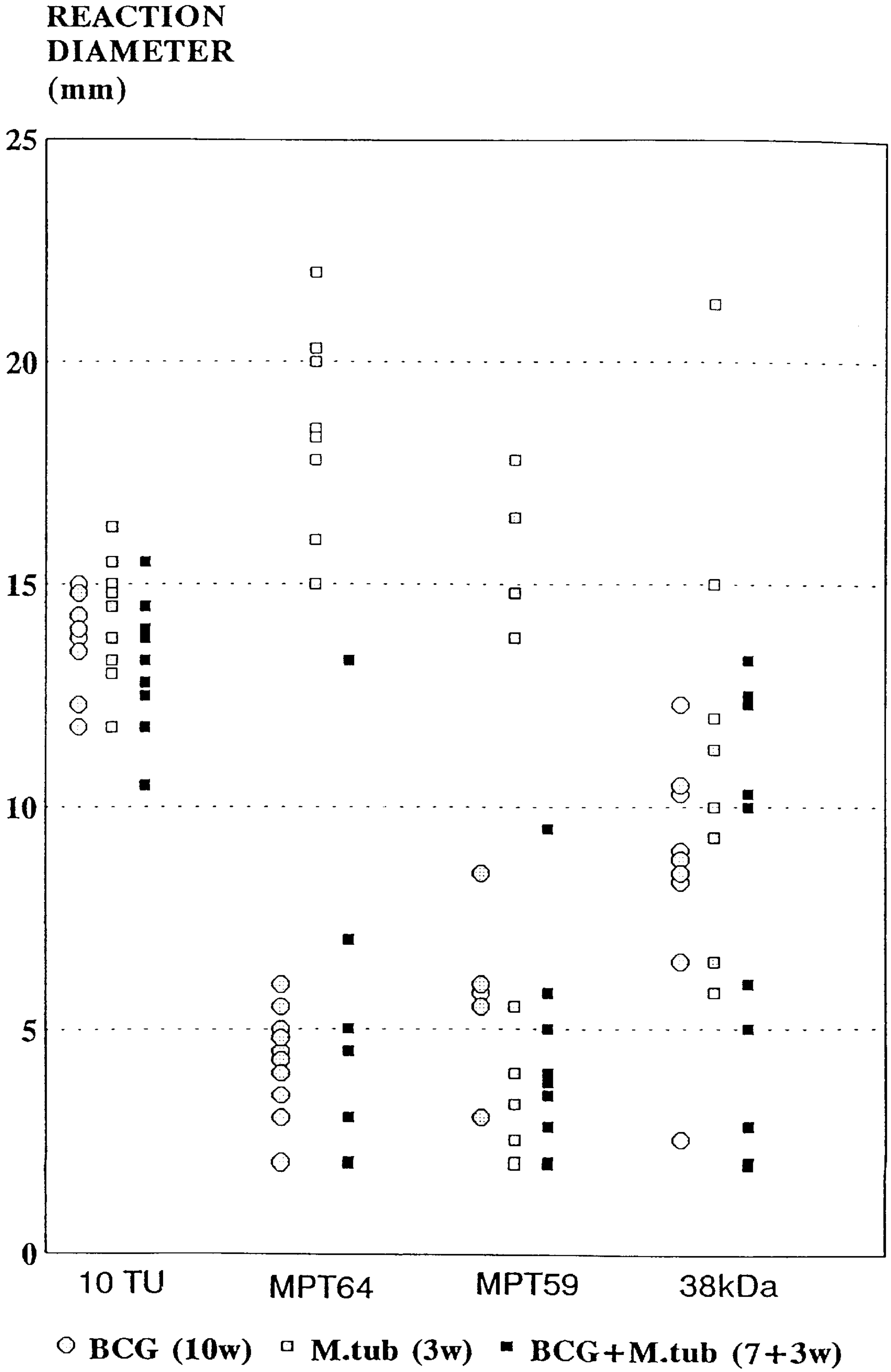

FIG. 8: The distribution of skin reactions in three groups of Ssc:AL guinea pigs.

Three groups of 10 Ssc:AL guinea pigs were infected with *M. tuberculosis* R1609 and/or BCG strain: Danish 1331. Group 1: BCG, skin tested after 10 weeks. Group 2: No BCG, skin tested 3 weeks after *M. tuberculosis* infection. Group 3: BCG, *M. tuberculosis* infection after 7 weeks, skin tested after 10 weeks. All groups were skin tested simultaneously with 1 μg of the purified antigens indicated and with 10 T.U. of tuberculin.

Figure 9:
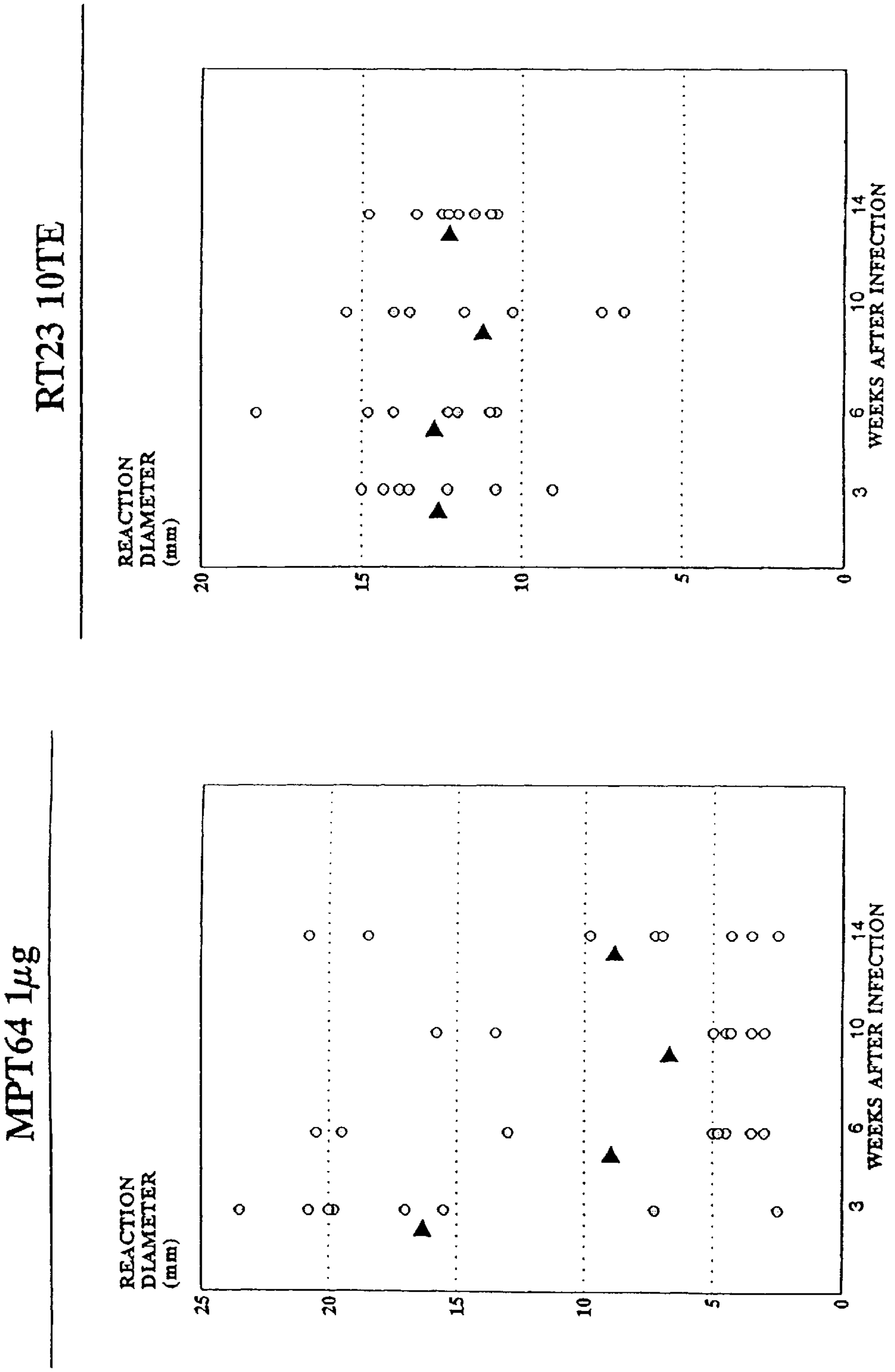

FIG. 9: The distribution and (solid arrows) of reactions in four groups of Ssc:AL guinea pigs.

Four groups of 7–8 Ssc:AL guinea pigs were infected with *M. tuberculosis* H37Rv. Three weeks later one group was skin tested and the others treated with antibiotics. The remaining groups were skin tested after 6, 10 and 14 weeks, one group at each time point. Skin tests were done with 1 μg of MPT64 and with 10 T.U. of tuberculin.

FIG. 10: Deletion mutants constructed as described in example 4.

Figure 11:
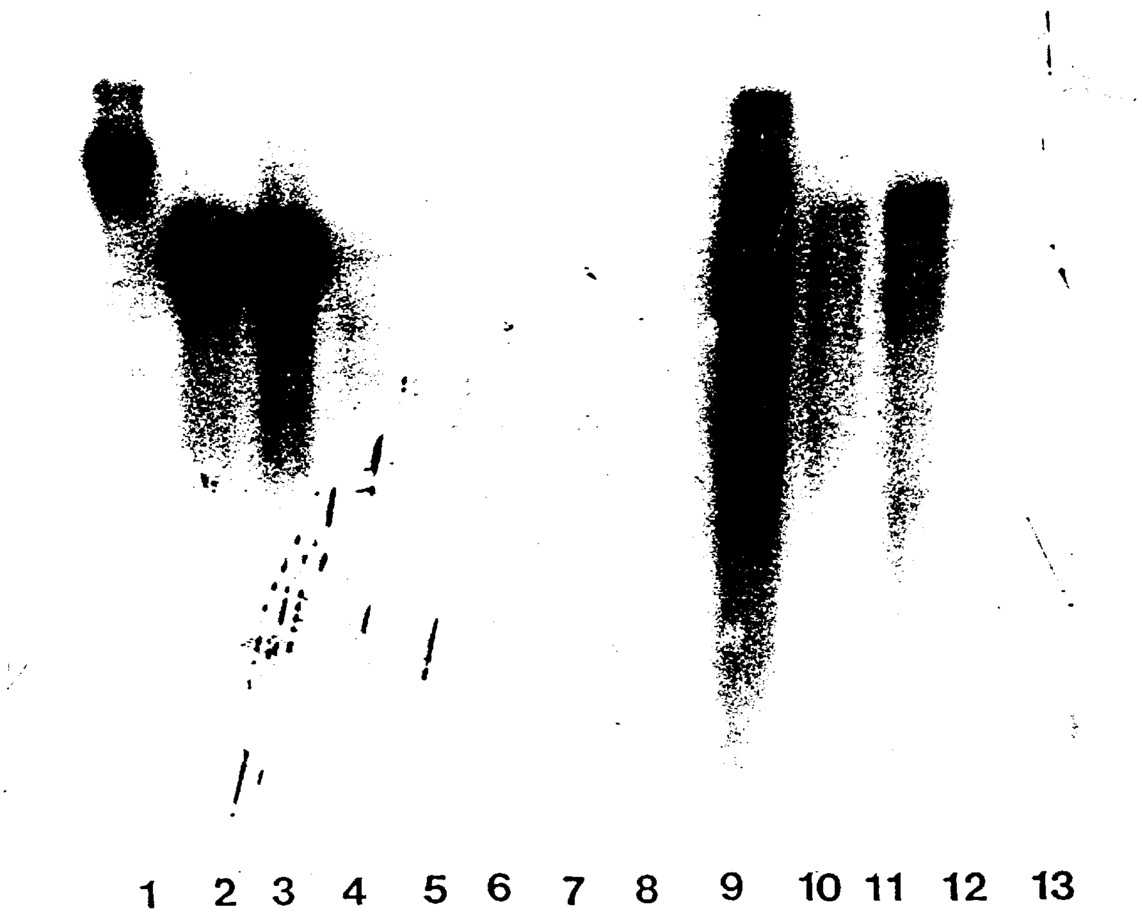

FIG. 11: Southern blot showing reaction with nick-translated recombinant MPT64 DNA.

Lane 1: *M. bovis* BCG Tokyo, lane 2: *M. bovis* BCG Moreau, lane 3: *M. bovis* BCG Russian, lane 4: *M. bovis* BCG Glaxo, lane 5: *M. bovis* BCG Pasteur, lane 6: *M. bovis* BCG Canadian, lane 7: *M. bovis* BCG Tice, lane 8: *M. bovis* BCG Copenhagen, lane 9: *M. tuberculosis* H37Rv, lane 10: *M. tuberculosis* H37Ra, lane 11: *M. tuberculosis* Erdman, lane 12: *M. leprae.*

Figure 12:
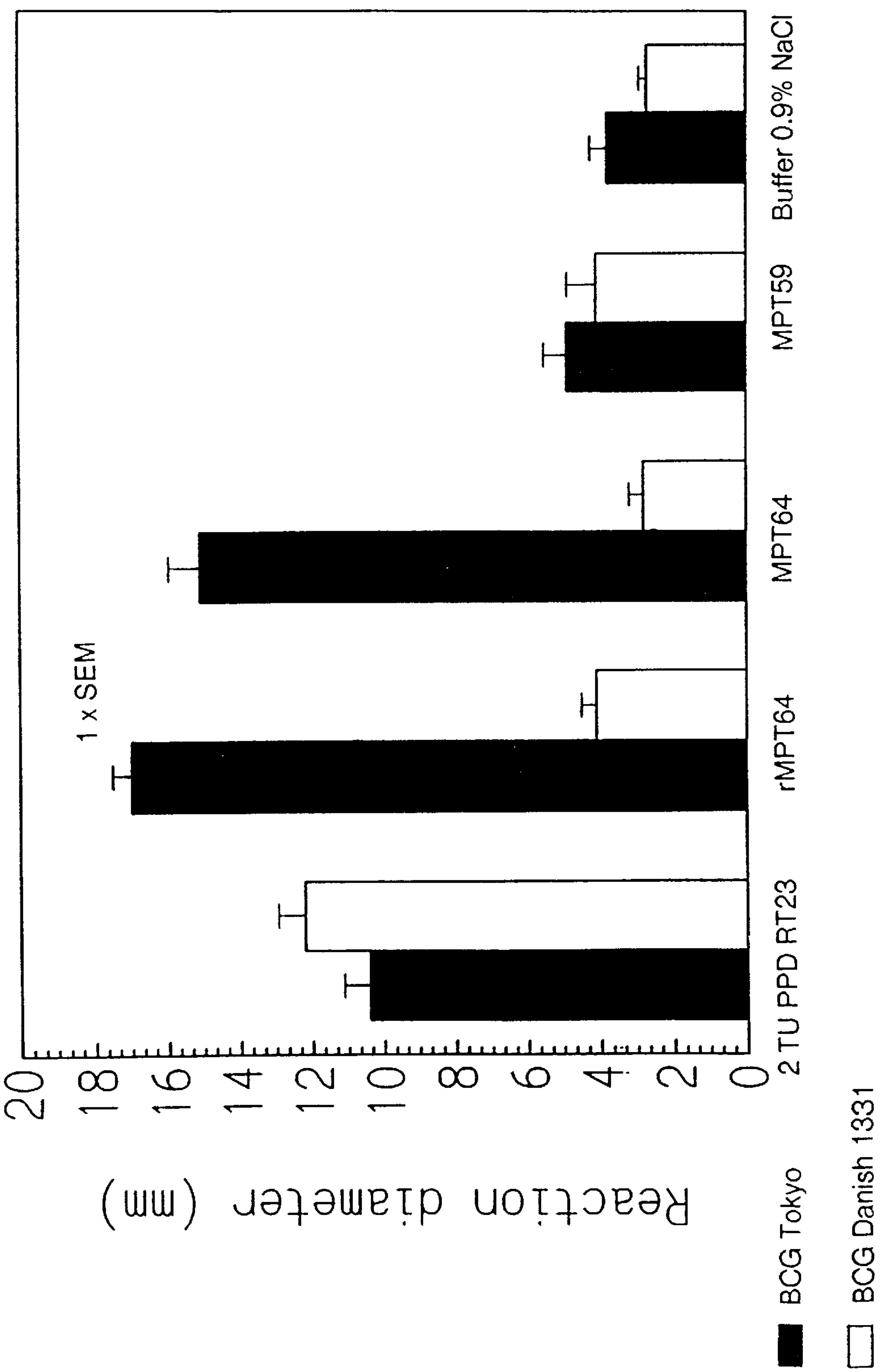

FIG. 12: The skin test inducing capacity of recombinant MPT64 (rMPT64) after removal of the fusion partner (the maltose binding protein).

The skin test inducing capacity of rMPT64 (0.1 μg) was compared to native MPT64 and PPD RT23 (2 TU) by assessing the reactions in groups (n=8) of outbred guinea pigs (Ssc:Al) immunized with either *M. bovis* BCG Tokyo (black bars) or *M. bovis* BCG Copenhagen (open bars). Skin testing was performed 4 weeks after immunization.

Figure 13:
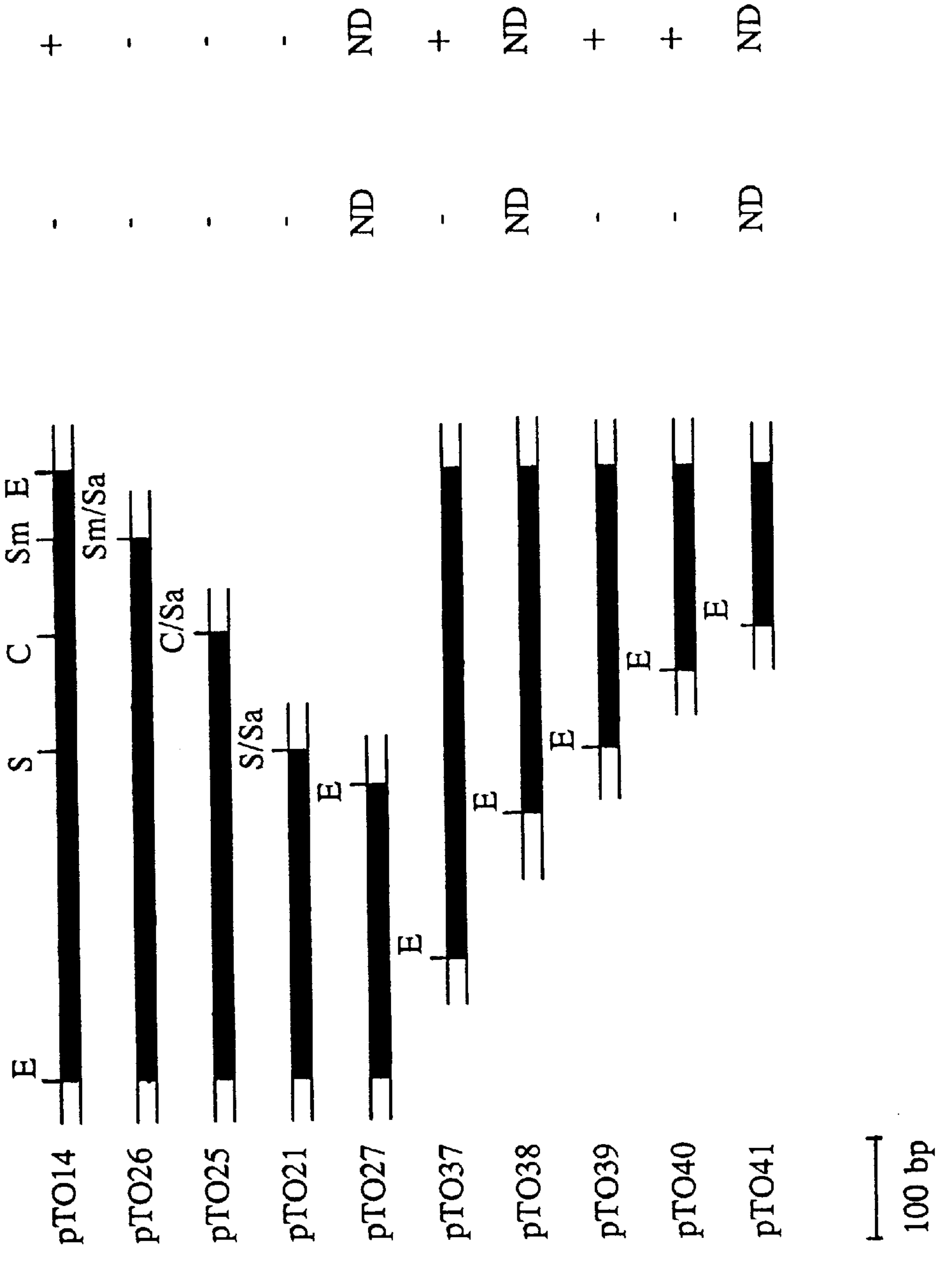

FIG. 13: Physical map of recombinant plasmids expressing various regions of mpt64 and skin reactions in guinea pigs to fusion proteins expressed by the plasmids.

Left part of the figure: The open bars are vector DNA. the closed bar is mpt64. The transcription of the gene is from left to right.

Right part of the figure: The reactivity against semi-purified recombinant fusion proteins established by skin testing of guinea pigs immunized with BCG Danish 1331 (left column) and BCG Tokyo (right column). A '+' indicates a skin reaction larger than 8 mm, a '–' indicates a skin reaction of less than 4 mm, and 'ND' indicates that the reaction not has been determined.

Figure 14:
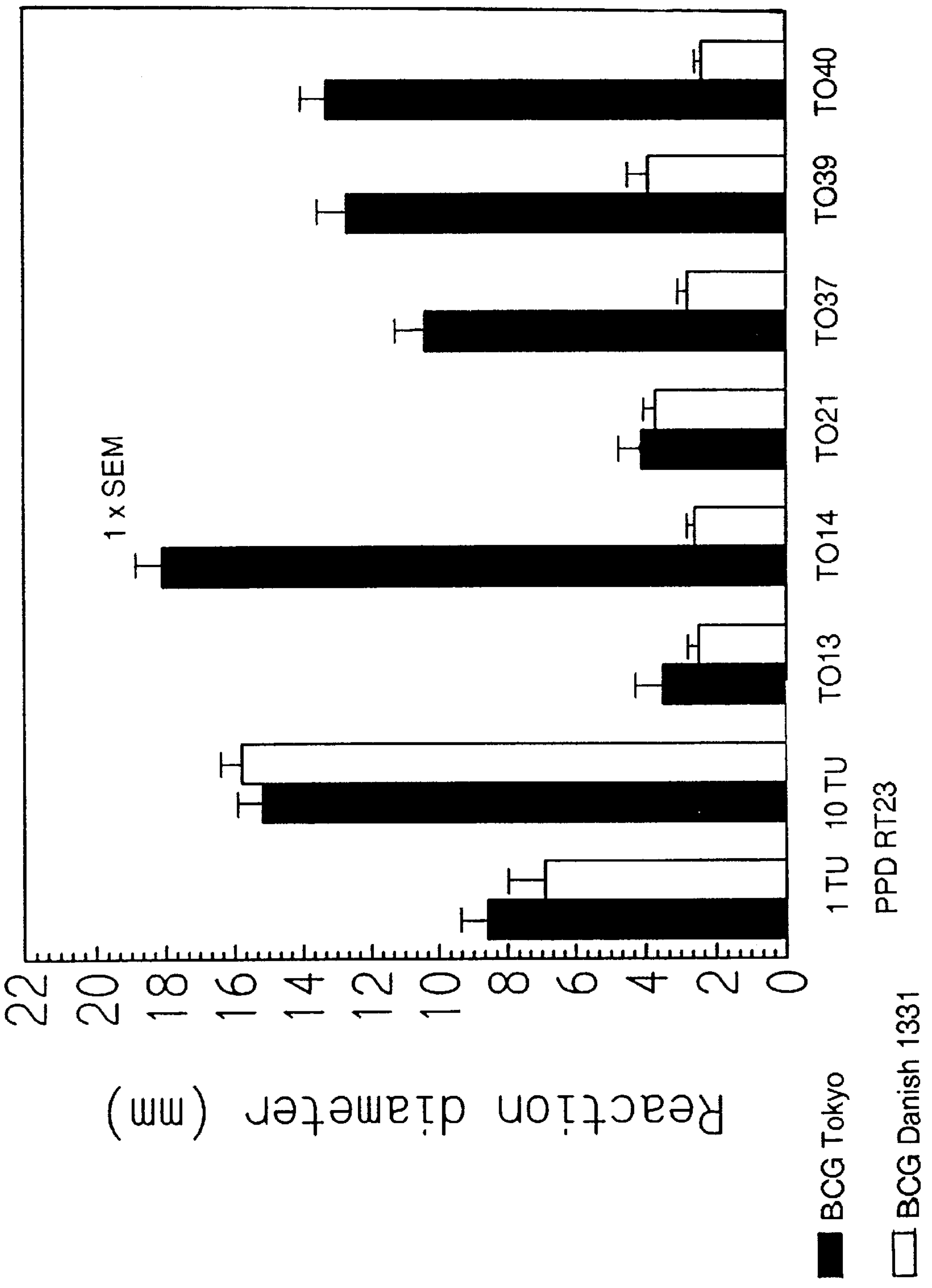

FIG. 14: Skin test reactions obtained in outbred guinea pigs by purified recombinant MPT64 fused to the maltose binding protein and mutated versions thereof lacking either parts of the N-terminus or the C-terminus of the protein as shown on the physical map in FIG. 13.

The reactions obtained by the maltose binding protein alone (produced and purified in the same way from the construct designated pTO13) did not exceed 4 mm. The concentration of contaminating lipopolysaccharide was determined by a conventional limulus assay and was found to comprise less than 0.05 ng/μg protein. It was concluded from this experiment that the biological activity of MPT64 is contained within the carboxyterminal one third of the protein (downstream from the endpoint of TO21). Restriction sites: C: ClaI; E. EcoRI; S: StuI; Sa: SalI: Sm: SmaI.

FIG. 15: Amino acid sequences of synthetic peptides used in skin tests in example 7.

The peptides are composed of 25 amino acids derived from the deduced amino acid sequence in FIG. 1.

Figure 16:
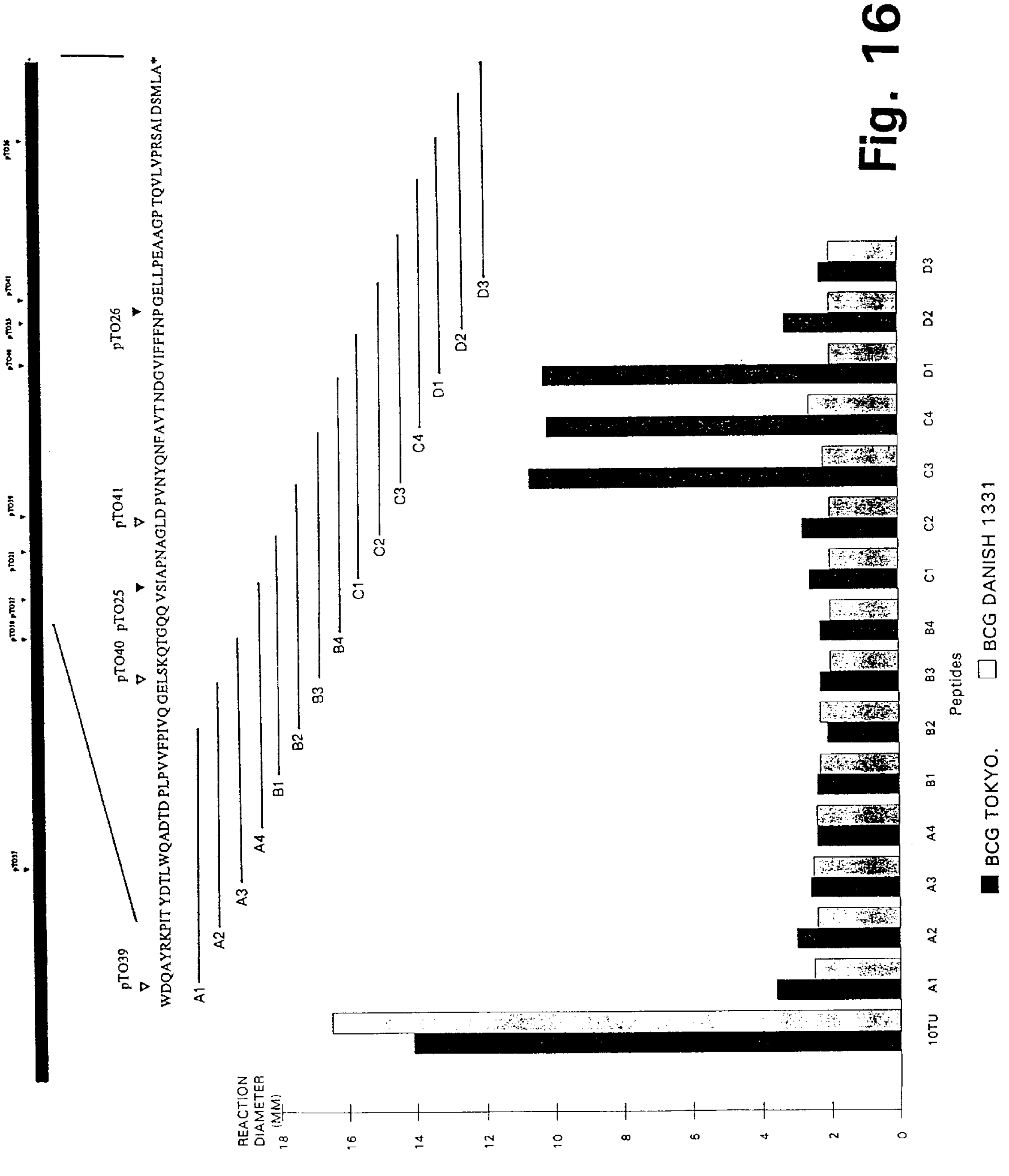

FIG. 16: Overlap of the synthetic peptides from FIG. 15 and skin test results after injection with the synthetic peptides.

The histogram shows the delayed type hypersensitivity reactions elicited in groups of outbred guinea pigs (n=8) after intradermal injections of 10 μg of synthetic peptides derived from the carboxyterminal one third of the MPT64. The guinea pigs were either immunized with *M. bovis* BCG Tokyo or BCG Danish 1331. The skin tests were performed three to four weeks after the immunization with the synthetic peptides of FIG. 15 and overlapping as indicated by solid lines marked: A1, A2, A3, A4, B1, B2, B3, B4, C1, C2, C3, C4, D1, D2, and D3. The reactions were read after 24 hours by two independent technicians.

Figure 17:
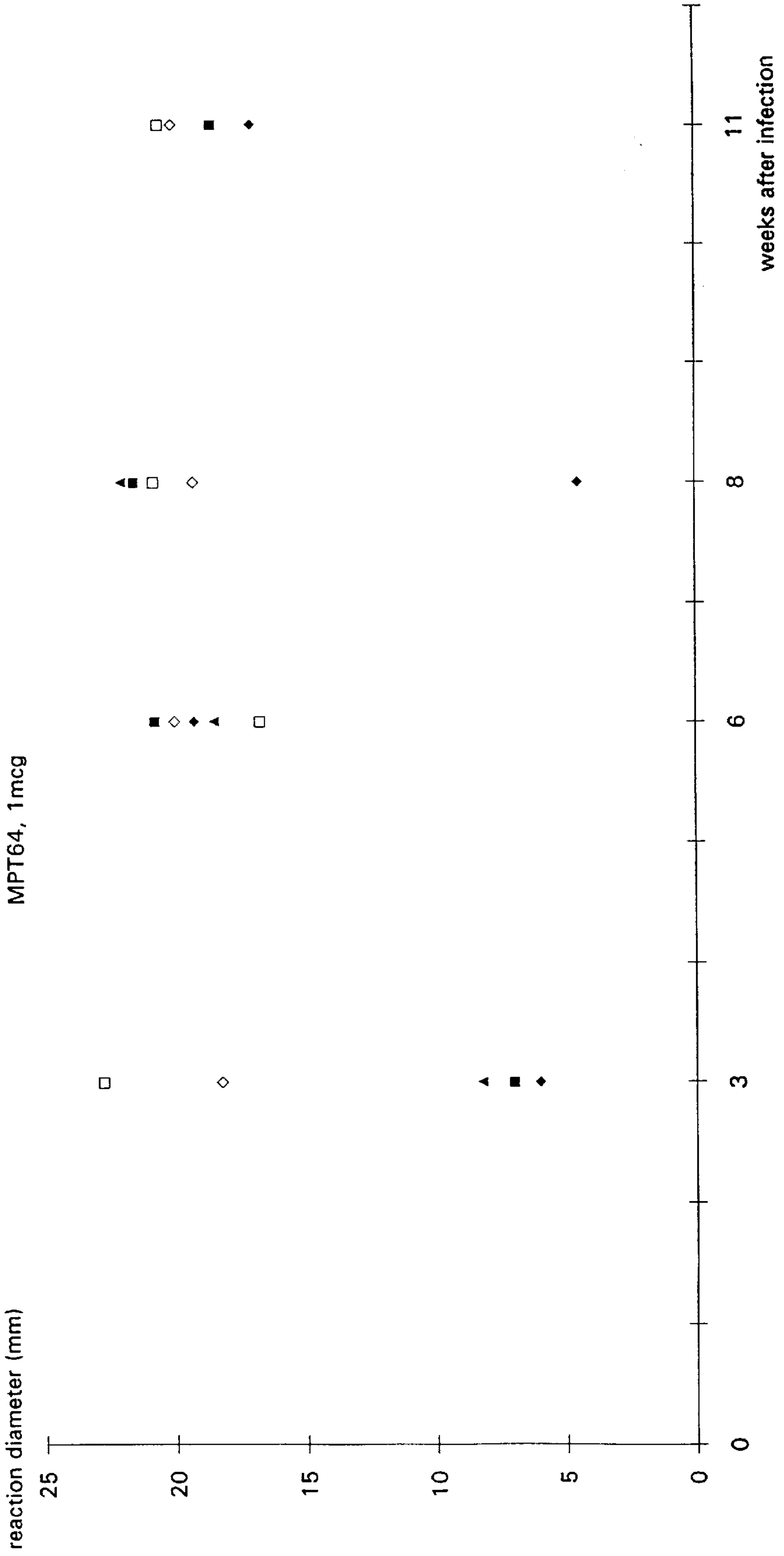

FIG. 17: Diameters in skin reaction following injection of 1 μg MPT64 in guinea pigs previously infected with aerosols of *M. tuberculosis* Erdman.

Figure 18:
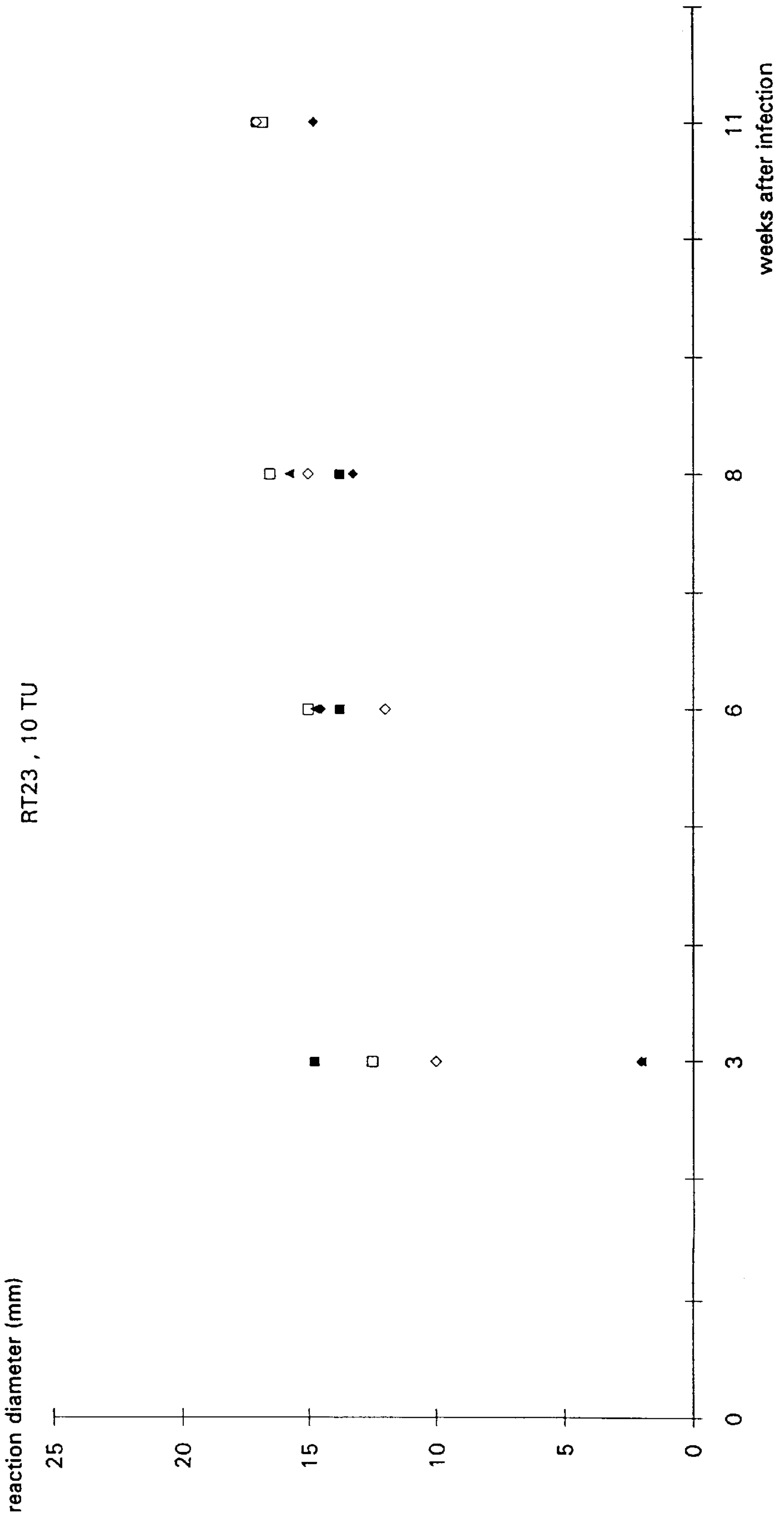

FIG. 18: Diameters in skin reaction following injection of 10 TU tuberculin in guinea pigs previously infected with aerosols of *M. tuberculosis* Erdman.

Each of the symbols in FIGS. 17 and 18, respectively, represents one individual; e.g., in FIG. 17 a solid diamond represents the skin reaction diameter in the same guinea pig at different time points after infection.

EXAMPLES

The following examples are intended to illustrate but not to limit the present invention.

The following methods are used generally in the following examples and are therefore discussed generally:

Hybridization of DNA

DNA, e.g. present on nitrocellulose filters, are wetted in 2×SSC (1×SSC: 0.15 M NaCl, 0.0015 M $Na_3$-citrate, pH 7.0) and placed in a heat-sealed plastic bag with pre-warmed (65° C.) prehybridization solution. Prehybridization takes place for 2 h at 65° C., the bag being gently shaken. The solution is exchanged with pre-warmed (65° C.) hybridization solution, a radioactive probe is added and hybridization is carried out at 65° C. for 18 h. The bag is gently shaken to ensure constant movement of the liquid over the nitrocellulose filters. After hybridization, a washing procedure is carried out.

The radioactive probe is prepared by use of known methods, e.g. as described by Sambrook et al., on the basis of the DNA sequence shown in SEQ ID NO: 1 or a part thereof, especially a coding part or an effective subsequence of the DNA sequence as defined above.

The prehybridization and hybridization solutions used are: 10×Denhardt's, 4×SSC, 0.1% SDS, 10 μg/ml polyA, 50 μg/ml of denatured DNA to be analyzed and the denatured (heat) radioactive probe. The filters are washed in pre-warmed (67° C.) solutions: 10×Denhardt, 2×SSC, 0.1% SDS for 2×15 min. and 1×SSC, 0.1% SDS for 4×15 min. The filters are air-dried and covered with Vita-Wrap, and X-ray film is exposed to the filters for 3 h to 3 weeks with and without intensifying screens.

EXAMPLE 1

Skin testing

MATERIALS AND METHODS

Guinea pigs

Outbred guinea pigs from strains Ssc:AL, Bfa/ZH/Kissleg and Hsd/Poc:DH were used. Additionally, two inbred strains NSD and IMM/R were used.

Bacterial strains

The following strains were used: *M. tuberculosis* H37Rv, *M. tuberculosis* R1609 (isolated from a Danish patient with lung tuberculosis), *M. tuberculosis* Erdman, *M. bovis* MNC27, *M. bovis* BCG strain: Danish 1331, *M. bovis* BCG Tokyo.

Infection and immunization of guinea pigs

When infected with strains of *M. tuberculosis* or virulent *M. bovis* guinea pigs were given $2.5\times10^3$ cfu in a volume of 0.1 ml in an ear vein. Infection by the same route (i.v.) with BCG was done with $2.5\times10^4$ cfu. Vaccinations with BCG were done with four intradermal (i.d.) injections on the abdomen of 0.1 ml of reconstituted BCG vaccine. BCG strain: Danish 1331 contained approximately $4\times10^6$ and BCG Tokyo $24\times10^6$ cfu per ml of the reconstituted preparations. Immunizations with killed bacteria were given 4×0.1 ml i.d. on the abdomen of a suspension of glutaraldehyde killed bacteria at 0.4 mg (semidry weight) per ml of paraffine oil (Marcol 52 (M52)).

Antiobiotic therapy

When indicated in the text, guinea pigs were given isoniazide (INH) (Merck) at 100 mg/l and rifabutin (R) (Farmitalia Carlo Erba) at 100 mg/l in the drinking water.

Bacterial enumeration

The number of viable bacteria in the spleens of infected mice was determined by plating double serial ten-fold dilutions of organ homogenates on Lowenstein-Jensen medium. Colonies were counted after 3 to 4 weeks of incubation. The results presented are geometric means within groups.

Antigens

Tuberculin PPD RT23 (Statens Seruminstitut) was used as a positive control in skin test experiments in sensitized guinea pigs.

MPT59 and MPT64 were prepared by S. Nagai as described by Nagai et al. (1991). *M. tuberculosis* H37Rv were cultured for 5 weeks on Sauton medium and the culture supernatant harvested by centrifugation. The supernatant was concentrated by precipitation with 80% ammonium sulphate. The concentrate was applied to a DEAE-Sepharose CL-6B (Pharmacia, Uppsala) column with 30 mM Tris hydrochloride buffer (pH 8.7) with 3% methylcellosolve. The proteins were eluted with a sodium chloride gradient. MPT59 and MPT64 is primarily contained in the fraction eluted with 110–140 mM sodium chloride. This fraction was applied to a DEAE-Sepharose CL-6B column in 30 mL Tris hydrochloride (pH 7.5) with 3 M urea, and was eluted with 50–90 mM NaCl. The eluate was divided and applied to two Sephacry S-200 HR columns in 10 mM Tris hydrochloride (pH 7.5) with 10% ethylene glycol and 300 mM NaCl. The relevant fractions from the S-200 runs containing MPT64 or MPT59, respectively, were applied to Phenyl-Sepharose CL-48 columns, the MPT64 fraction in 10 mM Tris hydrochloride (pH 7.5) and the MPT59 fraction in the same buffer with 50 mM ammonium sulphate (AS).

The MPT64 column was eluted with an AS gradient. The fraction 200 mM - 25 mM AS was applied to DEAE- Sepharose CL-6B in 30 mM Tris-HCl (pH 8.7). MPT64 was eluted with 60–90 mM NaCl.

The MPT59 column was washed with 10 mM Tris-HCl (pH 7.5) and eluted with 10 mM Tris-HCl (pH 8.7). The eluate containing MPT59 was applied to DEAE-Sepharose CL-6B in 30 mM Tris-HCl (pH 8.7). MPT59 was eluted with 80–110 mM NaCl.

The 38 kDa antigen was purified by affinity chromatography as described previously (Worsaae et al., 1987). *M. tuberculosis* H37Rv was grown on Sauton medium and the culture filtrate (CF) isolated by filtration. CF was precipitated twice with 80% ammonium sulphate, redissolved and dialysed against phosphate buffered saline (pH 7.4). The affinity column was prepared by coupling the HBT12 monoclonal antibody to CNBr activated Sepharose 4B (Pharmacia). CF was passed through the column at 1–5 mg/ml of phosphate buffered saline (pH 7.4) with 0.5 M NaCl and 0.05% Tween 20. After washing the antigen was eluted with 0.1 M glycine hydrochloride (pH 2.8) and dialysed against phosphate buffered saline (pH 7.4).

Skin tests

Guinea pigs were given i.d. injections on the shaven back of 0.1 ml physiological phosphate buffered saline (pH 7.4) containing the desired quantity of antigen. Guinea pigs were depilated on the back 24 h later and reactions were read by two independent readers, each measuring two transverse diameters of the erythemas. Reaction diameters are given as means corresponding to a single diameter.

Lymphocyte stimulation tests

Peripheral blood lymphocytes were isolated from blood drawn by cardiac puncture using EDTA as anticoagulant. Erythrocytes were removed by ficoll density gradient (d=1.09) centrifugation. Lymphocytes were washed twice, counted and the cell concentration adjusted to $2\times10^6$ cells/ml in RPMI 1640 with supplements including 5% FCS. Spleen lymphocytes were isolated by pressing spleens through a wire mesh. Erythrocytes were lysed by treatment with 0.84% $NH_4Cl$. The lymphocytes were washed twice and the cell concentration adjusted to $2\times10^6$ cells/ml of RPMI with supplements.

0.1 ml of cells were cultured with 0.1 ml of antigen or mitogen in triplicate for 6 days, the last 22 h in the presence of 1 $\mu$Ci $^3$H-thymidine. Cultures were harvested and incorporated $^3$H-thymidine counted in a scintillation counter. Results were expressed as stimulation indices using geometric means of triplicate cultures, the stimulation index being defined as the ratio between stimulated and non-stimulated cultures.

RESULTS

MPT64 skin tests distinguish infections with *M. tuberculosis* and BCG

Two separate experiments were carried out to compare skin reactivity to selected mycobacterial antigens in groups of Ssc:AL guinea pigs (GP's) infected i.v. or vaccinated i.d. with BCG strain: Danish 1331 to reactivity in animals infected with *M. tuberculosis* (H37Rv). Skin tests were applied 3 weeks after infection/vaccination. The results, which are summarized in FIG. 2, show that BCG as well as *M. tuberculosis* induce similar reactions to 10 T.U. of tuberculosis and to the 38 kDa antigen. In contrast, *M. tuberculosis* infection induces large reactions to MPT64 in the majority (approximately 70%) of GP's, but not in any BCG primed GP. The minority of *M. tuberculosis* infected GP's are, most likely for genetic reasons non-responders to MPT64. The majority of *M. tuberculosis* infected GP's are non-responders to MPT59.

Genetic restriction of MPT64 responses

The presence of non-responders to a diagnostic reagent in a human population is of course an issue of great concern.

To pursue this question, two additional outbred strains of GP's were infected with *M. tuberculosis* or BCG i.v. and skin tested as described above. The results (not shown) were similar to those obtained with Ssc:AL GP's, in particular a similar low frequency of non-responders was seen.

In another experiment, two inbred strains of GP's, NSD and IMM/R were infected with *M. tuberculosis* and skin tested. The results show that both strains are uniform responders to MPT64, but non-responders to MPT59 (FIG. 3).

Clinical experiments will clarify whether and to what extent humans are non-responders to these antigens.

Comparisons of MPT64 reactivity (in vivo and in vitro) in guinea pigs sensitized with living and killed *M. tuberculosis*

Because MPT64 and MPT59 are secreted proteins, it is relevant to compare reactivity in GP's sensitized with living and killed bacteria. Groups of GP's were infected with *M. tuberculosis,* BCG or immunized with killed *M. tuberculosis* in oil and skin tested 3 weeks later. The results show that similar tuberculin reactions were induced by the different sensitizations (FIG. 4). Positive skin reactions to MPT64 and MPT59 were, however, absent in GP's immunized with killed *M. tuberculosis,* and as seen previously in BCG-vaccinated GP's.

In a similar experiment groups of Ssc:AL GP's were sensitized by infection with *M. tuberculosis,* BCG i.d., BCG i.v., or immunized with killed *M. tuberculosis* in oil or (as a control) oil alone (M52). 3 weeks later peripheral blood and spleen lymphocytes were isolated and used for lymphocyte stimulation experiments. The results obtained were similar for both cell types. The results from peripheral blood cells shown in FIG. 5 demonstrate, with the exception of the control group, uniformly strong responses to tuberculin PPD and uniformly moderate responses to the 38 kDa antigen. In contrast, only lymphocytes from *M. tuberculosis* infected GP's reacted to MPT64, thus confirming the skin test results.

The results suggest that growth of *M. tuberculosis* is a prerequisite for development of MPT64 reactivity.

Skin reaction to MPT64 in *M. bovis* and *M. bovis* BCG Tokyo infected guinea pigs To extend the observations on bacterial species and strain specificity of MPT64, reactivity was compared in groups of GP's vaccinated with BCG strain: Danish 1331 and BCG Tokyo (FIG. 6) and in groups infected with *M. tuberculosis* or a virulent strain of *M. bovis* (FIG. 7).

The results show that vaccination with BCG Tokyo induces skin reactions to MPT64 and MPD70, but not MPT59 (FIG. 6). Vaccination with BCG strain: Danish 1331 did not induce reactions to these antigens. The difference in MPB70 reactivity between these BCG strains, which belong to different "families", has been described previously.

Comparison of reactivity to MPT64 and MPT59 in *M. bovis* and *M. tuberculosis* infected GP's show similar distribution of skin reactions in the groups. This suggests that MPT64 may be a useful diagnostic reagent in bovine tuberculosis.

MPT64 skin reactions in BCG vaccinated guinea pigs infected with *M. tuberculosis.* It is an important consideration in a diagnostic situation whether a BCG vaccinated individual subsequently infected with *M. tuberculosis* develops reactivity to MPT64 whether or not disease develops. Accordingly, three groups of GP's were given $2.5\times10^3$ cfu BCG strain: Danish 1331 and/or $2.5\times10^3$ cfu *M. tuberculosis* as shown below:

| | | | | |
|---|---|---|---|---|
| | BCG ↓ | - ↓ | Skin tests ↓ | |
| Group 1 | | | | → |
| | - ↓ | M. tub. ↓ | Skin tests ↓ | |
| Group 2 | | | | → |
| | BCG ↓ | M. tub. ↓ | Skin tests ↓ | |
| Group 3 | | | | → |
| | 0 ↓ | 7 ↓ | 10 ↓ | |
| Weeks | | | | → |

All guinea pigs were skin tested and spleens taken for counting of *M. tuberculosis* after 10 weeks. The results shown in FIG. 8 demonstrate that all groups of GP's develop similar tuberculin reactivity and that MPT64 gives reactions only in group 2. It thus appears that preinfection with BCG before *M. tuberculosis* infection prevents sensitization to MPT64.

The mean results from counting of *M. tuberculosis* were:

Group 1: 0 cfu/spleen

Group 2: $3\times10^3$ cfu/spleen

Group 3: $7.7\times10^5$ cfu/spleen

Thus, the preinfection with BCG has resulted in a 200-fold reduction of bacterial growth in the spleen. These results indicate that substantial growth of *M. tuberculosis* is a prerequisite for development of MPT64 reactivity in the GP, and make it likely that disease is likewise a prerequisite in a patient.

Persistency of MPT64 reactivity

Persistency of reactivity is an important parameter in the evaluation of a diagnostic reagent. To address this problem, 4 groups of GP's were infected with *M. tuberculosis* and 3 weeks later given isoniazide and rifabutin in the drinking water to prevent further growth of the bacteria. One group was skin tested after 3 weeks, one after 6, one after 10 and the last 14 weeks following constant throughout the observation period, whereas the reactivity to MPT64 drops rapidly to a low plateau level (FIG. 9).

These results suggest that MPT64 may have its prime use in the diagnosis of an acute infection rather than as an epidemiological tool.

Conclusion and comments

The present series of experiments suggests that MPT64 may be a suitable skin test reagent for diagnosis of tuberculosis, a reagent with a specificity not present in tuberculin preparations.

Another important issue for the general usefulness of the preparation is how long BCG Tokyo vaccinated persons retain their vaccine-induced MPT64 reactivity. If this reactivity has waned at a time they contract a tuberculosis infection, MPT64 will be a useful diagnostic reagent in such patients.

EXAMPLE 2

Cloning and expression of MPT64

DNA technology

Standard procedures were used for the preparation and handling of DNA (Maniatis, T., E. F. Fritsch, and J. Sambrook. 1989. Molecular Cloning. A laboratory manual. Cold Spring Harbor Laboratory, Cold Spring Harbor, N.Y.).

Synthesis and design of probes

Oligonucleotide primers were synthesized automatically with a DNA synthesizer (Applied Biosystems (ABI-391, PCR-mode)) and purified by ethanol precipitation. Four oligonucleotides were synthesized on the basis of the nucleotide sequence from MPB64 (Yamaguchi, R., K. Matsuo, A. Yamazaki, C. Abe, S. Nagai, K. Terasaka, and T. Yamada. 1989. Cloning and Characterization of the Gene for Imunogenic Protein MPB64 of *Mycobacterium bovis* BCG. Infect. Immun. 57:283–288), and five oligonucleotides were synthesized on the basis of the deduced nucleotide sequence from MPT64 in this study (Table 1). The oligonucleotides were engineered to include an EcoRI restriction enzyme site at the 5' end and at the 3' end by which a later subcloning was possible.

TABLE 1

Sequence of the MPT64 oligonucleotides

| Oligonucleotide | Sequences (5'-3') | Position |
|---|---|---|
| Sense | | |
| MPT64-1 | GAA TTC GCG CCC AAG ACC TAC TGC | 207 to 225 |
| MPT64-4 | GAT GCG AAT TCG AAA ATT ACA TCG CCC | 337 to 352 |
| MPT64-5 | GAT GCG AAT TCA AGG TCT ACC AGA ACG | 479 to 496 |
| MPT64-6 | GAT GCG AAT TCC AGG CCT ATC GCA AGC | 543 to 559 |
| MPT64-7 | GAT GCG AAT TCA GCA AGC AGA CCG GAC | 637 to 652 |
| MPT64-8 | GAT GCG AAT TCG ACC CGG TGA ATT ATC | 685 to 700 |
| MPT64-9 | CTC GAA TTC TGC TAG CTT GAG | 1 to 14 |
| Anti-sense | | |
| MPT64-2 | GAA TTC TAG GCC AGC ATC GAG TCG | 826 to 807 |
| MPT64-3 | GAA TTC CGG CGT TCT GGT AGA CC | 500 to 483 |

Oligonucleotides: MPT64-1, MPT64-2, MPT64-3, and MPT64-9 were constructed from the MPB64 sequence (Yamaguchi et al. 1989). The rest of the oligonucleotides were constructed after the nucleotide sequence obtained from MPT64 reported in this work. The Oligonucleotides are listed in SEQ ID NO: 3 to SEQ ID NO: 11. Nucleotides underlined are not contained in the nucleotide sequence of MPB64 or MPT64.

DNA cloning

MPT64 was cloned from *M. tuberculosis* H37Rv chromosomal DNA extracted and purified as described by Andersen et al. (Andersen Å. B., P. Andersen, L. Ljungquist 1992. Structure and Function of a 40,000 Molecular Weight Protein Antigen of *Mycobacterium tuberculosis.* Infect. Immun. 60, 2317–2323) by the use of the PCR technology as described by Innis et al. (Innis, M. A., D. H. Gelfand, J. J. Sninsky, and T. J. White. 1990. PCR Protocols. A Guide to Methods and Applications, pp. 253–258. Academic Press, Inc., San Diego, Calif.).

In brief, the standard amplifications were carried out in a Termal Reactor, Hybaid, Teddington, UK, by incubation of 100 ng of chromosomal *M. tuberculosis H*37Rv brought to a final volume of 37 $\mu$l with Milli Q water at 70° C. for 5 minutes and then cooled on wet ice for 10 minutes. 13 $\mu$l of PCR master mix was added. The PCR master mix contained: 192 mM KCl, 38.5 mM Tris/HCl, pH 8.3, 5.8 mM $MgCl_2$, 0.77 mM in each dNTP and 3.8 $\mu$M in each oligonucleotide primer. The reaction mixture were overlayed with 100 $\mu$l mineral oil. Denaturation of the DNA was carried out at 94° C. for 5 minutes. The reaction mix were brought to the annealing temperature, 60° C., 1.5 units AmpliTaq DNA polymerase (Perkin Elmer Cetus, Norwalk, Conn.) was added to the master mix. The amplifications were performed for 30 cycles, 72° C. for 3 minutes, 94° C. for 1 minute 20 seconds, 60° C. for 2 minutes. At the end of the cycles the primer extension step was carried out for 7 minutes.

10 $\mu$l of the PCR product was fractionated on 1.5% w/v agarose gel electrophoresis and visualized with ethidium bromide. Negative controls containing all PCR reagents except DNA were run in parallel with the samples.

The PCR product was cloned in the pCR1000 vector as described for the TA Cloning System (InVitrogen, San Diego, Calif.) and transformed *E. coli* INVaF' (EndA1, recA1, hsdR17 (r−k, m+k), supE44, λ-, thi-1, gyrA, relA1, ρ80 lacZΔM15Δ (lacZYA-argF9, deoR+, F') (InVitrogen, San Diego, Calif.).

Four oligonucleotides (Table 1) were constructed from the sequence of MPB64 (Yamaguchi et al. 1989) in expectation of some sequence homology between MPB64 and MPT64. Hereby were i) the structural gene of MPT64 and ii) the promoter region, the signal sequence and the N-terminal of MPT64 comprised. The PCR reactions gave two specific bands at i) 628 bp, and ii) 508 bp.

DNA Sequencing

The cloned 628 bp *M. tuberculosis* H37Rv PCR fragment, pTO1, containing the structural gene of MPT64, and the cloned 508 bp PCR fragment containing the promoter region and the signal peptide sequence, pTO3, was determined by the dideoxy chain termination method using a Sequenase DNA sequencing kit version 1.0 (U.S. Biochemical Corp., Cleveland, Ohio) according to the instructions provided. Both strands of the DNA were sequenced.

The nucleotide sequences of pTO01 and pTO03 of a gene coding MPT64 are shown in SEQ ID NO: 1 (and in FIG. 1).

Next, the nucleotide sequences were compared with the known amino acid sequence around N-terminus of MPT64 protein to find the GCG codon at position 208-210 corresponding to the N-terminal amino acid, Ala, of MPT64 (Andersen et al. 1991), and a TAG codon at position 823-825 is a termination codon. Therefore a structural gene coding for MPT64 protein derived from *M. tuberculosis H*37Rv was found to correspond to position 208-822 of the nucleotide sequence in SEQ ID NO: 1.

The nucleotide sequence for MPT64 contains only few nucleotide differences compared to MPB64. One nucleotide change is found in the structural gen of MPT64, at position 453 where a G is converted to an A. From the deduced amino acid this change occurs at a third position of the amino acid which does not lead to changes of the amino acid sequence. In the signal sequence at position 198 a G is converted to a C, also without any changes in the deduced amino acid composition. In the non-structural region of the promoter, the Shine-Dalgarno, etc. two differences occur, one addition at position 47 of a C, and one deletion of a G at position 100.

Thus, it is concluded that the structural gene for MPT64 consists of 615 bp and that the deduced amino acid sequence contains 205 amino acids with a calculated molecular weight of 22,433.

EXAMPLE 3

Subcloning of the MPT64 gene

An EcoRI site was engineered immediately 5' of the first codon of the gene so that only the coding region of the gene encoding the *M. tuberculosis* H37Rv 24 kD protein would be expressed, and an EcoRI site was incorporated right after the stop codon at the 3' end.

DNA of the recombinant plasmid pTO1 was cleaved at the EcoRI sites. The 628 bp fragment was purified from an agarose gel and subcloned into the EcoRI site of the pMAL-p expression vector (New England Ciolabs, Beverly, Mass.). Vector containing the gene fusion was transformed in the *E. coli* XL1-Blue (Bullock, W. O., J. M. Fernandez, and J. M. Short. 1987. XL1-Blue: A high efficiency plasmid transforming recA *Escherichia coli* strain with beta-galactosidase selection. BioTechniques 5: 376–379) for expression by the standard procedures for DNA manipulation.

The endpoints of the gen fusion were determined by the dideoxy chain termination method as described under the section DNA sequencing. Both strands of the DNA were sequenced.

EXAMPLE 4

Construction of MPT64 deletion mutants

DNA of the recombinant plasmid pTO1 was cleaved in the MPT64 gene at the ClaI, the StuI or the SmaI site (FIG. 11). The DNA was treated with the Klenow fragment of DNA Polymerase I (Gibco BRL, Life Technology A/S, Roskilde, Denmark) to make the ends blunt. Subsequently the DNA was digested with EcoRI, and the 327 bp EcoRI—StuI, the 459 bp EcoRI—ClaI, and the 542 bp EcoRI—SmaI fragments were purified from a 2% w/v agarose gel.

The pMAL-p vector was cleaved at the unique SalI site, and the DNA was treated with the Klenow fragment of DNA Polymerase I to make the end blunt. The DNA was afterwoards digested at the unique EcoRI site, and the large EcoRI—SalI fragment was purified from a 0.8% w/v agarose gel.

Additional one C-terminal deletion mutant was engineered by PCR using the primers MPT64-1 and MPT64-3 (Table 1). The 299 by EcoRI digested fragment was subcloned in pMAL-p.

The different construction possibilities were ligated. The ligated DNA was transformed into *E. coli* XL1- Blue and plated on Luria-Bertani agar with 50 $\mu$g/ml ampicillin, 12.5 $\mu$g/ml tetracycline, and 80 $\mu$g/ml 5-bromo-4-chloro-3-indolyl-β-D-galactoside (X-Gal). White colonies were picked randomly, and plasmid DNA was cleaved with BamHI and HindIII, and analysed by agarose gel electrophoresis to control determine the size of the mycobacterial insert.

Deletion mutants containing DNA of the right sites were sequenced by the dideoxy chain termination method as described under the section DNA sequencing to confirm the inframe fusion to malE in pMAL-p. Both strands of the DNA were sequenced in all the constructions.

To create deletion mutants from the N-terminal of the gene also, five oligonucleotides, MPT64-4, MPT64-5, MPT64-6, MPT64-7, and MPT64-8 (Table 1), containing an EcoRI site were engineered to create an inframe fusion with the malE of the pMAL-p vector by PCR as described in the DNA cloning section. The EcoRI digested PCR fragments were subcloned in the EcoRI site of the pMAL-p expression vector. A vector containing the gene fusion was transformed into the *E. coli* XL1-Blue for expression by standard procedures for DNA manipulation. To confirm that the deletions of all five constructions were in frame with the malE gene in pMAL-p, both strands were sequenced by the dideoxy chain termination method as described under the section DNA sequencing.

A physical map of a number of these deletion mutants can be seen in FIG. 13.

EXAMPLE 5

Preparation and purification of recombinant MPT64 and truncated version of MPT64

Recombinant antigens were prepared in accordance with instructions provided by New England Biolabs. Briefly, XL1-Blue cells containing the fusion plasmid of interest were grown in Luria-Bertani media with 50 μg/ml ampicillin and 12.5 μg/ml tetracycline to $A_{600\ nm}$ app. 0.5, and the production of the fusion protein was induced with 0.3 mM isopropylthiogalactoside (IPTG) at 37° C. for 2 hours. The pelleted XL1-Blue cells were frozen at −20° C. overnight in the column buffer (20 mM TRIS/HCl, pH 7.4, 200 mM NaCl, 1 mM EDTA, and 1 mM DTT) and thawed at 4° C. followed by incubation with 1 mg/ml lysozyme on ice for 30 min, followed by sonication in the column buffer for 200 sec in periods of 10 sec followed by a pause of 30 sec. After centrifugation at 9.000 g, the fusion proteins were purified from the crude extracts by affinity chromatography on amylose resin column. The MPB fusion protein binds to amylose. After extensive washes of the column, the fusion proteins were eluted with 10 mM maltose.

Aliquots of the fractions were analyzed on 10% SDS-PAGE (Laemmli, U. K. 1970. Cleavage of structural proteins during the assembly of the head of bacteriophage T4. Nature 277, 680–685). Fractions containing the fusion protein of interest were pooled and dialysed against 4×100 volumes of PBS, pH 7.3, and the protein concentration was determined as described by Bradford.

Southern blotting

Mycobacterial genomic DNA was prepared as described by Andersen et al., 1992. The Mycobacterium strains used in this study are listed in Table 2.

*M. leprae* Armadillo-derived chromosomal DNA was obtained from M. Colston, Mill Hill, London, England.

Four μg of chromosomal DNA was digested with EcoRI, elctrophoresed in an 0.8% agarose gel, and transferred onto Gene-Screen Plus membranes (NEN Research Products, Boston, Mass.). Hybridization was performed at 65° C. in an aqueous solution containing 1% SDS, 1M NaCl, 10% dextran sulfate, 100 μg of denatured salmon sperm DNA per ml, and a (α-$^{32}$P) dCTP nick-translated MPT64 DNA probe.

The distribution of MPT64 in different *M. tuberculosis* substrains, *M. bovis* BCG substrains, and in *M. leprae* by the use of the 628 bp MPT64 nucleotide fragment from pTO1 as a prove in Southern blot experiments is shown in FIG. 11. The probe hybridized to EcoRI fragments of app. 14 kb for *M. tuberculosis* H37Rv, of app. 12 kb for *M. tuberculosis* H37Ra and *M. tuberculosis* Erdman, of app. 20 kb for *M. bovis* BCG Tokyo, and of app. 9.5 kb for *M. bovis* BCG Moreau and *M. bovis* BCG Russian, but the probe did not hybridize to any EcoRI fragments from *M. bovis* BCG Glaxo, *M. bovis* BCG Pasteur, *M. bovis* BCG Canadian, *M. bovis* BCG Tice, *M. bovis* BCG strain; Danish 1331, and *M.laprae.*

TABLE 2

Mycobacterial strains used in this study

| No. | Strain | Source |
|---|---|---|
| 1 | *M. tuberculosis* H37Rv | ATCC* No. 27294 |
| 2 | *M. tuberculosis* Erdman | Obtained from A. Lazlo, Canada. |
| 3 | *M. tuberculosis* H37Ra | ATCC* No. 25177 |
| 4 | *M. bovis* Calmette Guerin | Copenhagen BCG Laboratory, SSI+ |
| 5 | *M. bovis* Calmette Guerin | Tokyo# |
| 6 | *M. bovis* Calmette Guerin | Moreau# |
| 7 | *M. bovis* Calmette Guerin | Russian# |
| 8 | *M. bovis* Calmette Guerin | Glaxo# |
| 9 | *M. bovis* Calmette Guerin | Pasteur# |
| 10 | *M. bovis* Calmette Guerin | Canadian# |
| 11 | *M. bovis* Calmette Guerin | Tice# |
| 12 | *M. leprae* Armadillo-derived | Obtained from M J Colston, England |

*American Type Culture Collection, USA.
+Statens Seruminstitut, Denmark.
#WHO International Laboratory for Biological Standards, Statens Seruminstitut, Denmark.

EXAMPLE 6

Skin testing of guinea pigs with rMPT64

The immunological potential of MPT64 was assessed by the following experiment:

A group of outbred guinea pigs (strain Ssc:Al) was immunized with eith *M. bovis* BCG Danish 1331 or with *M. bovis* BCG Tokyo. All guinea pigs were skin tested with 0.1 μg purified rMPT64 (recombinant MPT64), native MPT64, and 2 T.U. of tuberculin as described by Andersen et al. (1991) in Scand. J. Immun. 59: 365–372. The skin reactions to tuberculin were used as a positive control of the ummunization. Skin reactions in the guinea pigs to the purified recombinant antigen is shown in FIG. 12.

rMPT64 elicited Dth reactions in the guinea pigs sensitized with *M. bovis* BVD Tokyo, the skin reactions are comparable to those obtained by purified MPT64, no skin reactions were seen in guinea pigs sensitized with *M. bovis* BCG Danish 1331. In conclusion rMPT64 is as suitable as purified MPT64 as a skin test reagent, and rMPT64 has, like MPT64, a specificity superior to tuberculin preparations.

EXAMPLE 7

T-cell epitope mapping on rMPT64 fusion proteins by skin testing guinea pigs

In order to map specific T-cell epitopes on rMPT64 fusion proteins by skin testing, a group of outbred guinea pigs (strain SSc:Al) was immunized with either *M. bovis* BCG Danish 1331 or *M. bovis* BCG Tokyo. The sensitized guinea pigs were skin tested with C- and N-terminally truncated versions of rMPT64 as MBP fusion proteins (cf. example 4).

The fusion proteins were semi-purified by affinity chromatography on an amylose resin column followed by FPLC (Fast Performance Liquid Chromatography) over an anion exchange column (Mono Q) as described above. Aliquots of the fractions were analyzed on 10% SDS-PAGE. Fractions containing semi-purified recombinant fusion proteins were pooled and dialysed extensively against physiological saline before use. The skin test experiments with the recombinant fusion proteins indicated that the specific T-cell epitope is located within the sequence encoded by TO40 (FIGS. 13 and 14).

In order to further confirm the localization of the T-cell epitope, similar experiments were performed using synthetic peptides derived from the carboxy terminal end of MPT64 instead of deletion mutants. The amino acid sequences of the peptides employed can be seen in FIG. 15, and the results of the skin tests can be seen from FIG. 16.

As can be seen from FIG. 16, the reactive synthetic fragments are C3, C4, and D1. These results confirm that the location of the T-cell epitope is found between the amino acids 186–215 in SEQ ID NO: 2.

EXAMPLE 8

Kinetics of the skin inducing capacity of MPT64 compared to PPD RT23 in aerosol infected guinea pigs In order to establish how early in the course of infection guinea pigs are converted to MPT64-positives, the following experiment was carried out:

Four groups of guinea pigs (n=5) were exposed to aerosols of *M. tuberculosis* Erdman at doses giving rise to an average of 5 primary tuberculous lesions per lung. Skin testings were performed after 3, 6, 8, and 11 weeks after inhalation, cf. FIG. 17. All the animals tested 6 weeks after exposure mounted a positive skin test reaction to MPT64. This result is in agreement with the conventional tuberculin skin testings, cf. FIG. 18.

The conclusion is that reactivity towards MPT64 has an onset at approximately the same stage after infection with mycobacteria as the onset of the tuberculin reaction.

EXAMPLE 9

Comparison of specific, skin test inducing activity of native MPT64 with MPT64 molecules which have been chemically modified by pretreatment with either glutaraldehyde or formaldehyde It is contemplated that reactivity of MPT64 or analogues thereof will be enhanced if it is possible to maintain a high local concentration of the antigen at the injection site. Thereby is obtained that the intensity of the reaction is increased and the persistence at the injection site prolonged. One possible strategy which is expected to have this result is the use of homopolymers of MPT64 made by chemical treatment with the denaturing agents glutaraldehyde or formaldehyde.

In order to test whether this strategy is likely to lead to the expected result, it is planned to perform the following experiment:

40 μg of native MPT64 is incubated at 37° C. for 8 days in the presence of variouys concentrations of glutaraldehyde or formaldehyde (0.005M, 0.025M, and 0.125M) in a total volume of 1.0 ml PBS. The samples are subsequently dialysed against 100 ml of PBS four times. The protein concentration in the final sample preparation is then checked again before being injected into guinea pigs, which have been immunized with either BCG Tokyl or BCG Danish 1331. The reactions should be read after 24, 48, and 72 hours.

LIST OF REFERENCES

Andersen, Å. B., Andersen, P., Ljungqvist, L. Infection and Immunity 60: 2317–2323, 1992.

Andersen, Å. B., Ljungqvist, L., Haslφv, K., Bentzon, M. W. Scand. J. Immunol. 34: 365–372, 1991.

Bullock, W. O., Fernandez, J. M., Short, J. M. Biotechniques 5: 376–379, 1987.

Innis, M. A., Gelfand, D. H., Sninsky, J. J., White, T. J. Academic Press, 253–258, 1990.

Laemnli, U. K. Nature 277: 680–685, 1970.

Lotte, A., Wasz-Höckert, O., Poisson, N., Dumitrescu, N., Verron, M. Couvet, E. Adv. Tuberc. Res. 21: 107–193, 1984.

Maniatis, T., Fritsch, Sambrook, J. Molecular cloning. A Laboratory Manual. Second edition. Cold Spring Harbor Laboratory Press 1989

Nagai, S. Wiker, H. G., Harboe, M., Kinomoto, M. Infection and Immunity 59: 372–382, 1991.

Worsaae, A., Ljungqvist, L., Haslφv, K., Heron, I., Bennedsen, J. Infection and Immunity 55: 2922–2927, 1987.

Yamaguchi, R. Matsuo, K., Yamazaki, A., Abe, C., Nagai, S., Terasaka, K. Yamada, T. Infection and Immunity 57: 283–288, 1989.

What is claimed is:

1. A kit comprising:

(A) a BCG vaccine against tuberculosis, and (B) at least one diagnostic test comprising a pharmaceutical composition comprising a polypeptide, wherein:

(i) the polypeptide has a length of at least 12 amino acid residues, and the polypeptide has a sequence comprising at least 12 amino acid residues from a polypeptide of a mycobacterium of the tuberculosis complex (*Mycobacterium tuberculosis, Mycobacterium africanum* and *Mycobacterium bovis*), and (ii) lymphoid cells previously primed with virulent mycobacteria belonging to the tuberculosis complex (*Mycobacterium tuberculosis, Mycobacterium africanum* and *Mycobacterium bovis*) are capable of reacting with the polypeptide and (iii) lymphoid cells previously primed with a vaccine against tuberculosis are not capable of reacting with the polypeptide, and (iv) a positive response is indicative of having or having had tuberculosis, and (v) a negative response is indicative of not having or not having had tuberculosis.

2. A kit according to claim 1, wherein the pharmaceutical composition comprises a homopolymer of the polypeptide.

3. A kit according to claim 2, wherein the homopolymer is produced by introduction of at least one cyteine residue in the N-terminal region of the polypeptide.

4. A kit according to claim 1, wherein the pharmaceutical composition comprises a heteropolymer of the polypeptide.

5. A kit according to claim 4, wherein the heteropolymer comprises the polypeptide coupled to a carrier or vehicle.

6. A kit according to claim 4, wherein the heteropolymer comprises the polypeptide coupled to another mycobacterial protein.

7. A kit according to claim 1, wherein the polypeptide has been post-translationally modified.

8. A kit according to claim 1, wherein the positive response is a positive skin response which appears 1–4 days after injection.

9. A kit according to claim 1, wherein the positive response is a positive skin response between 0.5 cm and 4.0 cm in diameter.

10. A kit according to claim 1, wherein the polypeptide has an amino acid sequence comprising the amino acid sequence SEQ ID NO: 2.

11. A kit according to claim 1, wherein the polypeptide is encoded by a DNA molecule having a nucleotide sequence comprising the nucleotide sequence SEQ. ID NO: 1.

12. A kit according to claim 1, wherein the polypeptide has been modified in order to abolish or delete sensitizing epitopes.

13. A kit according to claim 1, wherein the polypeptide has been modified by denaturing procedures.

14. A kit according to claim 1, wherein the polypeptide comprises MPT64.

15. A kit according to claim 1, wherein the pharmaceutical composition comprises at least two different polypeptides.

16. A ket according to claim 15 comprising a first polypeptide comprising MPT64 and a second polypeptide comprising MPT59.

17. A kit according to claim 14, wherein the pharmaceutical composition comprises 0.05 to 20 μg of the polypeptide.

18. A kit comprising:

(A) a BCG vaccine against tuberculosis, wherein said BCG vaccine does not contain MPT64 or MPT59 or a fragment thereof having a length of at least 12 amino acids from MPT64 or MPT59, and (B) at least one diagnostic test comprising a pharmaceutical composition comprising a polypeptide, wherein:

(i) the polypeptide comprises MPT64, or MPT59, or MPT64 and MPT59, or a fragment of MPT64 or MPT59, or a fragment of MPT64 and MPT59; said fragment having a length of at least 12 amino acid residues from MPT64 and/or MPT59, and (ii) lymphoid cells previously primed with virulent mycobacteria belonging to the tuberculosis complex (*Mycobacterium tuberculosis, Mycobacterium africanum* and *Mycobacterium bovis*) are capable of reacting with the polypeptide and (iii) lymphoid cells previously primed with a vaccine against tuberculosis are not capable of reacting with the polypeptide, and (iv) a positive response is indicative of having or having had tuberculosis, and (v) a negative response is indicative of not having or not having had tuberculosis.

19. A method of diagnosing tuberculosis caused by *Mycobacterium tuberculosi, Mycobacterium africanum* or *Mycobacterium bovis* in an individual susceptible thereto, comprising:

exposing immune cells of the individual to a pharmaceutical composition comprising a polypeptide:

having a length of at least 12 amino acid residues, wherein the polypeptide has a sequence comprising at least 12 amino acid resiudes from a polypeptide of a mycobacterium of the tuberculosis complex (*Mycobacterium tuberculosis, Mycobacterium africanum* and *Mycobacterium bovis*), and with which lymphoid cells previously primed with virulent mycobacteria belonging to the tuberculosis complex (*Mycobacterium tuberculosis, Mycobacterium africanum* and *Mycobacterium bovis*) are capable of reacting and with which lymphoid cells previously primed with a BCG vaccine against tuberculosis are not capable of reacting, wherein a positive response is indicative of the individual having or having had tuberculosis, and a negative response is indicative of the individual not having or not having had tuberculosis.

20. A method of diagnosing tuberculosis caused by *Mycobacterium tuberculosis, Mycobacterium africanum* or *Mycobacterium bovis* in an individual susceptible thereto, comprising:

exposing immune cells of the individual to a pharmaceutical composition comprising a polypeptide:

having a length of at least 12 amino acid residues, wherein the polypeptide has a sequence comprising at least 12 amino acid residues from a polypeptide of a mycobacterium of the tuberculosis complex (*Mycobacterium tuberculosis, Mycobacterium africanum* and *Mycobacterium bovis*), and with which lymphoid cells previously primed with virulent mycobacteria belonging to the tuberculosis complex (*Mycobacterium tuberculosis, Mycobacterium africanum* and *Mycobacterium bovis*) are capable of reacting and with which lymphoid cells previously primed with a BCG vaccine against tuberculosis are not capable of reacting, wherein a positive response is indicative of the individual having or having had tuberculosis, and a negative response is indicative of the individual not having or not having had tuberculosis, and the polypeptide is as in the dit of claim 2–7, 10,11–13, 14–16, 17, or 18.

21. A method of diagnosing tuberculosis caused by *Mycobacterium tuberculosis, Mycobacterium africanum* or *Mycobacterium bovis* in an individual susceptible thereto, comprising:

exposing immune cells of the individual to a pharmaceutical composition comprising a polypeptide comprising MPT64, or MPT59, or MPT64 and MPT59, or a fragment of MPT64 or MPT59 or a fragment of MPT64 and MPT59; said fragment having a length of at least 12 amino acid residues from MPT64 and/or MPT59, and with which lymphoid cells previously primed with virulent mycobacteria belonging to the tuberculosis complex (*Mycobacterium tuberculosis, Mycobacterium africanum* and *Mycobacterium bovis*) are capable of reacting and with which lymphoid cells previously primed with a BCG vaccine against tuberculosis are not capable of reacting, wherein the BCG vaccine does not contain MPT64 or MPT59 or a fragment thereof having a length of at least 12 amino acids from MPT64 or MPT59, a positive response is indicative of the individual having or having had tuberculosis, and a negative response is indicative of the individual not having or not having had tuberculosis.

22. The method of claim 19 wherein the pharmaceutical composition comprises a homopolymer and/or a heteropolymer of the polypeptide.

23. The method of claim 19 wherein the polypeptide comprises: MPT64; or MPT59; or a polypeptide encoded by a nucleic acid molecule comprising MPT64-4, MPT64-5, MPT64-6, MPT64-7, MPT64-8; or a polypeptide comprising amino acids 186–215 of SEQ ID NO:2; or a polypeptide comprising an amino acid sequence as set forth in SEQ ID NO:2; or a polypeptide comprising a polypeptide encoded by the sequence set forth in SEQ ID NO:1.

24. An isolated polypeptide consisting of an amino acid sequence as set forth in SEQ ID NO:2.

25. The isolated polypeptide according to claim 24, which has been modified in order to abolish or delete sensitizing epitopes.

26. The isolated polypeptide according to claim 24 containing at least one T-cell epitope.

27. An isolated polypeptide consisting of the amino acid sequence 186–215 in SEQ ID NO:2.

28. The kit of claim 1 wherein the polypeptide comprises a polypeptide encoded by a nucleic acid molecule comprising MPT64-4, MPT64-5, MPT64-6, MPT64-7, MPT64-8; or the polypeptide comprises amino acids 186–215 of SEQ ID NO:2.

29. A method of producing an isolated polypeptide as defined in claim 24, the method comprising sequentially linking component amino acids to form the polypeptide.

30. A kit according to claim 2, wherein the homopolymer comprises at least two copies of the peptide.

31. A kit according to claim 7, wherein the polypeptide has been post-translationally acylated, post-translationally glycosylated, or post translationally acylated and glycosylated.

32. A kit according to claim 8, wherein the positive skin response appears 2–3 days after injection.

33. A kit according to claim 9, wherein the positive skin response is between 1.0 cm and 3.0 cm in diameter.

34. A kit according to claim 18, wherein the polypeptide comprises MPT64 or MPT59.

35. A kit according to claim 13, wherein the denaturing procedures are selected from the group consisting of autoclaving, and treatment with formaldelyde or glutaraldehyde.

36. A kit according to claim 17 wherein the pharmaceutical composition comprises 0.5 to 2.0 μg of the polypeptide.

37. A kit according to claim 17 wherein the pharmaceutical composition comprises 0.75 to 1.5 μg of the polypeptide.

38. The method of claim 29 of producing an isolated polypeptide comprising solid or liquid phase peptide synthesis.

39. A kit comprising:

(A) a BCG vaccine against tuberculosis comprising an amount of a BCG vaccine against tuberculosis, and (B) at least one diagnostic test comprising a pharmaceutical composition comprising a polypeptide, wherein (i) the polypeptide comprises a polypeptide encoded by a DNA molecule having a nucleotide sequence comprising the nucleotide sequence SEQ ID NO: 1 and (ii) lymphoid cells previously primed with virulent mycobacteria belonging to the tuberculosis complex (*Mycobacterium tuberculosis, Mycobacterium africanum* and *Mycobacterium bovis*) are capable of reacting with the polypeptide and (iii) lymphoid cells previously primed with the vaccine are not capable of reacting with the polypeptide, and (iv) intradermal injection of the polypeptide at a location of injection elicits a skin reaction having a diameter of at least 0.5 cm in an individual previously sensitized with virulent mycobacteria belonging to the tuberculosis complex and, (v) a positive response is indicative of the person having or having had tuberculosis, and (vi) a negative response is indicative of the person not having or not having had tuberculosis.

40. The kit of claim 1 wherein the diagnostic test is a diagnostic skin test for intradermal injection, the positive response is a positive response at the location of injection, and the negative response is a negative response at the location of injection.

41. The kit of claim 18 wherein the BCG vaccine is BCG strain: Danish 1331.

42. The method of claim 19 wherein exposing immune cells is by intradermal injection, the positive response is a positive skin response at the location of injection, and the negative response is a negative skin response at the location of injection.

43. The method of claim 21 wherein the BCG vaccine is BCG strain: Danish 1331.

44. The method of claim 31 wherein the polypeptide is from a mycobacterium belonging to the tuberculosis complex.

45. The method according to claim 20, wherein the BCG vaccine is from BCG strain: Danish 1331.

46. The method according to claim 20, wherein the polypeptide comprises a polypeptide encoded by a nucleic acid molecule comprising MPT64-4, MPT64-5, MPT64-6, MPT64-7, MPT64-8; or the polypeptide comprises amino acids 186–215 of SEQ ID NO:2.

47. The kit of claim 39 wherein the diagnostic test is a diagnostic skin test for intradermal injection, the positive response is a positive response at the location of injection, and the negative response is a negative response at the location of injection.

48. The method of claim 20 wherein exposing immune cells is by intradermal injection, the positive response is a positive skin response at the location of injection, and the negarive response is a negative skin response at the location of injection.

49. The kit of claim 1 wherein the polypeptide comprises a polypeptide from a mycobacterium of the tuberculosis complex (*Mycobacterium tuberculosis, Mycobacterium africanum* and *Mycobacterium bovis*).

50. The method according to claim 19 wherein the polypeptide comprises a polypeptide from a mycobacterium of the tuberculosis complex (*Mycobacterium tuberculosis, Mycobacterium africanum* and *Mycobacterium bovis*).

* * * * *

SEQUENCE LISTING

```
(1) GENERAL INFORMATION:

   (iii) NUMBER OF SEQUENCES: 11


(2) INFORMATION FOR SEQ ID NO: 1:

     (i) SEQUENCE CHARACTERISTICS:
          (A) LENGTH: 826 base pairs
          (B) TYPE: nucleic acid
          (C) STRANDEDNESS: double
          (D) TOPOLOGY: linear

    (ii) MOLECULE TYPE: DNA (genomic)

    (vi) ORIGINAL SOURCE:
          (A) ORGANISM: Mycobacterium tuberculosis
          (B) STRAIN: H37Rv

    (ix) FEATURE:
          (A) NAME/KEY: CDS
          (B) LOCATION: 139..822

    (ix) FEATURE:
```

-continued

```
          (A) NAME/KEY: sig_peptide
          (B) LOCATION: 139..207

    (ix) FEATURE:
          (A) NAME/KEY: -10_signal
          (B) LOCATION: 27..32

    (ix) FEATURE:
          (A) NAME/KEY: -35_signal
          (B) LOCATION: 51..56

    (xi) SEQUENCE DESCRIPTION: SEQ ID NO: 1:

TCTGCTAGCT TGAGTCTGGT CAGGCATCGT CGTCAGCAGC GCGATGCCCC TATGTTTGTC     60

GTCGACTCAG ATATCGCGGC AATCCAATCT CCCGCCTGCG CCGGCGGTGC TGCAAACTAC    120

TCCCGGAGGA ATTTCGAC GTG CGC ATC AAG ATC TTC ATG CTG GTC ACG GCT      171
                    Val Arg Ile Lys Ile Phe Met Leu Val Thr Ala
                      1               5                  10

GTC GTT TTG CTC TGT TGT TCG GGT GTC GCC ACG GCC GCG CCC AAG ACC      219
Val Val Leu Leu Cys Cys Ser Gly Val Ala Thr Ala Ala Pro Lys Thr
             15                  20                  25

TAC TGC GAG GAG TTG AAA GGC ACC GAT ACC GGC CAG GCG TGC CAG ATT      267
Tyr Cys Glu Glu Leu Lys Gly Thr Asp Thr Gly Gln Ala Cys Gln Ile
         30                  35                  40

CAA ATG TCC GAC CCG GCC TAC AAC ATC AAC ATC AGC CTG CCC AGT TAC      315
Gln Met Ser Asp Pro Ala Tyr Asn Ile Asn Ile Ser Leu Pro Ser Tyr
     45                  50                  55

TAC CCC GAC CAG AAG TCG CTG GAA AAT TAC ATC GCC CAG ACG CGC GAC      363
Tyr Pro Asp Gln Lys Ser Leu Glu Asn Tyr Ile Ala Gln Thr Arg Asp
 60                  65                  70                  75

AAG TTC CTC AGC GCG GCC ACA TCG TCC ACT CCA CGC GAA GCC CCC TAC      411
Lys Phe Leu Ser Ala Ala Thr Ser Ser Thr Pro Arg Glu Ala Pro Tyr
                 80                  85                  90

GAA TTG AAT ATC ACC TCG GCC ACA TAC CAG TCC GCG ATA CCA CCG CGT      459
Glu Leu Asn Ile Thr Ser Ala Thr Tyr Gln Ser Ala Ile Pro Pro Arg
             95                 100                 105

GGT ACG CAG GCC GTG GTG CTC AAG GTC TAC CAG AAC GCC GGC GGC ACG      507
Gly Thr Gln Ala Val Val Leu Lys Val Tyr Gln Asn Ala Gly Gly Thr
        110                 115                 120

CAC CCA ACG ACC ACG TAC AAG GCC TTC GAT TGG GAC CAG GCC TAT CGC      555
His Pro Thr Thr Thr Tyr Lys Ala Phe Asp Trp Asp Gln Ala Tyr Arg
    125                 130                 135

AAG CCA ATC ACC TAT GAC ACG CTG TGG CAG GCT GAC ACC GAT CCG CTG      603
Lys Pro Ile Thr Tyr Asp Thr Leu Trp Gln Ala Asp Thr Asp Pro Leu
140                 145                 150                 155

CCA GTC GTC TTC CCC ATT GTG CAA GGT GAA CTG AGC AAG CAG ACC GGA      651
Pro Val Val Phe Pro Ile Val Gln Gly Glu Leu Ser Lys Gln Thr Gly
                160                 165                 170

CAA CAG GTA TCG ATA GCG CCG AAT GCC GGC TTG GAC CCG GTG AAT TAT      699
Gln Gln Val Ser Ile Ala Pro Asn Ala Gly Leu Asp Pro Val Asn Tyr
            175                 180                 185

CAG AAC TTC GCA GTC ACG AAC GAC GGG GTG ATT TTC TTC TTC AAC CCG      747
Gln Asn Phe Ala Val Thr Asn Asp Gly Val Ile Phe Phe Phe Asn Pro
        190                 195                 200

GGG GAG TTG CTG CCC GAA GCA GCC GGC CCA ACC CAG GTA TTG GTC CCA      795
Gly Glu Leu Leu Pro Glu Ala Ala Gly Pro Thr Gln Val Leu Val Pro
    205                 210                 215

CGT TCC GCG ATC GAC TCG ATG CTG GCC TAGA                             826
Arg Ser Ala Ile Asp Ser Met Leu Ala
220                 225

(2) INFORMATION FOR SEQ ID NO: 2:
```

-continued (i) SEQUENCE CHARACTERISTICS:
(A) LENGTH: 228 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO: 2:

```
Val Arg Ile Lys Ile Phe Met Leu Val Thr Ala Val Val Leu Leu Cys
  1               5                  10                  15

Cys Ser Gly Val Ala Thr Ala Ala Pro Lys Thr Tyr Cys Glu Glu Leu
             20                  25                  30

Lys Gly Thr Asp Thr Gly Gln Ala Cys Gln Ile Gln Met Ser Asp Pro
         35                  40                  45

Ala Tyr Asn Ile Asn Ile Ser Leu Pro Ser Tyr Tyr Pro Asp Gln Lys
     50                  55                  60

Ser Leu Glu Asn Tyr Ile Ala Gln Thr Arg Asp Lys Phe Leu Ser Ala
 65                  70                  75                  80

Ala Thr Ser Ser Thr Pro Arg Glu Ala Pro Tyr Glu Leu Asn Ile Thr
                 85                  90                  95

Ser Ala Thr Tyr Gln Ser Ala Ile Pro Pro Arg Gly Thr Gln Ala Val
            100                 105                 110

Val Leu Lys Val Tyr Gln Asn Ala Gly Gly Thr His Pro Thr Thr Thr
        115                 120                 125

Tyr Lys Ala Phe Asp Trp Asp Gln Ala Tyr Arg Lys Pro Ile Thr Tyr
    130                 135                 140

Asp Thr Leu Trp Gln Ala Asp Thr Asp Pro Leu Pro Val Val Phe Pro
145                 150                 155                 160

Ile Val Gln Gly Glu Leu Ser Lys Gln Thr Gly Gln Gln Val Ser Ile
                165                 170                 175

Ala Pro Asn Ala Gly Leu Asp Pro Val Asn Tyr Gln Asn Phe Ala Val
            180                 185                 190

Thr Asn Asp Gly Val Ile Phe Phe Phe Asn Pro Gly Glu Leu Leu Pro
        195                 200                 205

Glu Ala Ala Gly Pro Thr Gln Val Leu Val Pro Arg Ser Ala Ile Asp
    210                 215                 220

Ser Met Leu Ala
225
```

(2) INFORMATION FOR SEQ ID NO: 3:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO: 3:

GAATTCGCGC CCAAGACCTA CTGC 24

(2) INFORMATION FOR SEQ ID NO: 4:

(i) SEQUENCE CHARACTERISTICS:
(A) LENGTH: 27 base pairs
(B) TYPE: nucleic acid
(C) STRANDEDNESS: single
(D) TOPOLOGY: linear -continued (ii) MOLECULE TYPE: DNA (synthetic)

(xi) SEQUENCE DESCRIPTION: SEQ ID NO: 4:

GATGCGAATT CGAAAATTAC ATCGCCC 27

(2) INFORMATION FOR SEQ ID NO: 5:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO: 5:

GATGCGAATT CAAGGTCTAC CAGAACG 27

(2) INFORMATION FOR SEQ ID NO: 6:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO: 6:

GATGCGAATT CCAGGCCTAT CGCAAGC 27

(2) INFORMATION FOR SEQ ID NO: 7:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO: 7:

GATGCGAATT CAGCAAGCAG ACCGGAC 27

(2) INFORMATION FOR SEQ ID NO: 8:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO: 8:

GATGCGAATT CGACCCGGTG AATTATC 27

(2) INFORMATION FOR SEQ ID NO: 9:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO: 9:

-continued

```
CTCGAATTCT GCTAGCTTGA G                                               21


(2) INFORMATION FOR SEQ ID NO: 10:

     (i) SEQUENCE CHARACTERISTICS:
          (A) LENGTH: 24 base pairs
          (B) TYPE: nucleic acid
          (C) STRANDEDNESS: single
          (D) TOPOLOGY: linear

    (ii) MOLECULE TYPE: DNA (synthetic)

   (iii) ANTI-SENSE: YES

    (xi) SEQUENCE DESCRIPTION: SEQ ID NO: 10:

GAATTCTAGG CCAGCATCGA GTCG                                            24


(2) INFORMATION FOR SEQ ID NO: 11:

     (i) SEQUENCE CHARACTERISTICS:
          (A) LENGTH: 23 base pairs
          (B) TYPE: nucleic acid
          (C) STRANDEDNESS: single
          (D) TOPOLOGY: linear

    (ii) MOLECULE TYPE: DNA (synthetic)

   (iii) ANTI-SENSE: YES

    (xi) SEQUENCE DESCRIPTION: SEQ ID NO: 11:

GAATTCCGGC GTTCTGGTAG ACC                                             23
```